(12) United States Patent
Bossmann et al.

(10) Patent No.: US 10,376,599 B2
(45) Date of Patent: Aug. 13, 2019

(54) NANOPLATFORMS FOR ARGINASE, INDOLEAMINE 2,3-DIOXYGENASE AND TRYPTOPHAN 2,3-DIOXYGENASE DETECTION BY POSTTRANSLATIONAL MODIFICATION

(71) Applicant: Kansas State University Research Foundation, Manhattan, KS (US)

(72) Inventors: Stefan H. Bossmann, Manhattan, KS (US); Deryl L. Troyer, Manhattan, KS (US); Aruni P. Malalasekera, Manhattan, KS (US); Hongwang Wang, Manhattan, KS (US); Sebastian O. Wendel, Manhattan, KS (US); Gaohong Zhu, Yunnan (CN)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/559,543

(22) PCT Filed: Mar. 18, 2016

(86) PCT No.: PCT/US2016/023188
§ 371 (c)(1),
(2) Date: Sep. 19, 2017

(87) PCT Pub. No.: WO2016/149637
PCT Pub. Date: Sep. 22, 2016

(65) Prior Publication Data
US 2018/0099057 A1    Apr. 12, 2018

Related U.S. Application Data

(60) Provisional application No. 62/135,366, filed on Mar. 19, 2015.

(51) Int. Cl.
*A61K 38/00* (2006.01)
*A61K 49/00* (2006.01)
*G01N 33/573* (2006.01)
*C12Q 1/26* (2006.01)
*C12Q 1/34* (2006.01)

(52) U.S. Cl.
CPC ...... *A61K 49/0093* (2013.01); *A61K 49/0032* (2013.01); *A61K 49/0036* (2013.01); *A61K 49/0056* (2013.01); *C12Q 1/26* (2013.01); *C12Q 1/34* (2013.01); *C12Y 113/11011* (2013.01); *C12Y 113/11052* (2013.01); *C12Y 305/03001* (2013.01); *G01N 33/573* (2013.01)

(58) Field of Classification Search
CPC ............ A61K 49/0032; A61K 49/0036; A61K 49/0056; A61K 49/0093; C12Q 1/26; C12Q 1/34; C12Y 113/11011; C12Y 113/11052; C12Y 305/03001; G01N 33/573

See application file for complete search history.

(56) References Cited

U.S. PATENT DOCUMENTS

| | | |
|---|---|---|
| 2009/0297689 A1 | 12/2009 | Edens et al. |
| 2011/0014125 A1 | 1/2011 | Bossmann et al. |
| 2011/0223657 A1 | 9/2011 | Kaper et al. |
| 2013/0323187 A1 | 12/2013 | Fasel et al. |

FOREIGN PATENT DOCUMENTS

WO    2002102834    12/2002

OTHER PUBLICATIONS

The International Search Report and Written Opinion dated Jul. 1, 2016, in OCT/US2016/023188, filed Mar. 18, 2016.
Seegers, Nicole, "High-Throughput Fluorescence-Based Screening Assays for Tryptophan Catabolizing Enzymes," Journal of Biomolecular Screening, Jun. 6, 2016.
Pilotte, Luc "Reversal of tumoral immune resistance by inhibition of tryptophan 2,3-dioxygenase," PNAS Feb. 14, 2012, pp. 2497-2502; vol. 109, No. 7.
Nau, Werner M. "Substrate-Selective Supramolecular Tandem Assays: Monitoring Enzyme Inhibition of Arginase and Diamine Oxidase by Fluorescent Dye Displacement from Calixarene and Cucurbituril Macrocycles," J. Am. Chem. Soc. 2009, May 22, 2009, pp. 11558-11570.
Tomek, Petr, "Formation of an N-formylkynurenine-derived fluorophore and its use for measuring indoleamine 2,3-dioxygenase 1 activity," Anal Bioanal Chem. Jan. 12, 2013, vol. 405, pp. 2515-2524.

*Primary Examiner* — Thomas S Heard
(74) *Attorney, Agent, or Firm* — Hovey Williams LLP

(57) ABSTRACT

A nanoplatform assembly for detection of arginase, indoleamine 2,3-dioxygenase 1, and/or tryptophan 2,3-dioxygenase. The nanoplatform comprises an oligopeptide, which is used as a linker between two particles. More preferably, the linker is comprised of an oligopeptide containing a substrate for the target enzyme, where the substrate is chemically or physically modified by the target enzyme (but not cleaved). A central particle with a plurality of oligopeptide-tethered detectable particles and a plurality of directly attached detectable particles is described. Posttranslational modification of the oligopeptide leads to changes in the detectable signals from the first and/or second particles in the nanoplatform, which can be correlated to enzyme activity and concentration.

21 Claims, 14 Drawing Sheets

Specification includes a Sequence Listing.

NANOPLATFORMS FOR ARGINASE, INDOLEAMINE 2,3-DIOXYGENASE AND TRYPTOPHAN 2,3-DIOXYGENASE DETECTION BY POSTTRANSLATIONAL MODIFICATION

CROSS-REFERENCE TO RELATED APPLICATIONS

The present application is the National Stage of International Patent Application No. PCT/US2016/023188, filed Mar. 18, 2016, which claims the priority benefit of U.S. Provisional Patent Application Ser. No. 62/135,366, filed Mar. 19, 2015, entitled NANOPLATFORMS FOR ARGINASE, INDOLEAMINE 2,3-DIOXYGENASE AND TRYPTOPHAN 2,3-DIOXYGENASE DETECTION BY POSTTRANSLATIONAL MODIFICATION, each of which is incorporated by reference in its entirety herein.

FEDERALLY SPONSORED RESEARCH OR DEVELOPMENT

This invention was made with government support under #1159966 awarded by the National Science Foundation. The United States government has certain rights in the invention.

SEQUENCE LISTING

The following application contains a sequence listing in computer readable format (CRF), submitted as a text file in ASCII format entitled "SequenceListing_47219-PCT," created on Mar. 18, 2015, as 5 KB. The content of the CRF is hereby incorporated by reference.

BACKGROUND OF THE INVENTION

Field of the Invention

The present invention relates to nanoplatforms for detection of enzymatic activity through posttranslational modification of peptide linkages.

Description of Related Art

Arginase (AGN) metabolizes L-arginine to L-ornithine and urea. Besides its fundamental role in the hepatic urea cycle, arginase is a key player in the immune system. In humans, arginase I is constitutively expressed in polymorphonuclear neutrophils, released during inflammation and responsible for the down-regulation of nitric oxide synthesis by depleting arginine. Arginase-mediated L-arginine depletion is capable of suppressing T cell immune responses, leading to inflammation-associated immune-suppression. Arginase II, which is expressed by macrophages, is known to be up-regulated in tumor-associated macrophages.

Indoleamine 2,3-dioxygenase 1 (IDO1) is a tryptophan-catabolizing enzyme. It is overexpressed by a broad range of solid tumors. IDO1 is a proximal biomarker for cancer progression and associated with immunosuppression. IDO1 is broadly expressed and regulated by interferon-γ (IFN-γ). Its substrates comprise L-tryptophan, D-tryptophan, 5-hydroxy-tryptophan, tryptamine, and serotonin.

Tryptophan 2,3-dioxygenase (TDO) has a similar biological function than IDO1. However, TDO is constitutively expressed at high levels in the liver, where it regulates systemic tryptophan levels. It is also significantly expressed in (human) tumors. It is specific for L-tryptophan.

SUMMARY OF THE INVENTION

The present invention is broadly concerned with a nanoplatform assembly for detecting the presence of an active enzyme in a sample. The nanoplatform generally comprises a central carrier particle; a first particle; a second particle; and an oligopeptide linkage connecting the central carrier particle and the second particle. The first particle is directly attached to the central carrier particle. The oligopeptide linkage comprises a substrate sequence for the enzyme, which is modifiable by the active enzyme.

Also described herein are methods for detecting the presence of an active enzyme in a sample from a mammal. The methods generally comprise contacting a fluid sample from the mammal with a nanoplatform assembly according to any of the embodiments described herein, wherein the second particle is characterized as having a detectable signal. The nanoplatform assembly is exposed to an energy source to generate the detectable signal from the second particle. Changes (if any) of the detectable signal are discerned during contact of the nanoplatform with the fluid sample, wherein these changes correspond to the active enzyme activity in the sample.

A composition is also described that comprises a nanoplatform assembly according any of the embodiments described herein and a pharmaceutically-acceptable carrier.

Further methods are described for detecting the presence of an active enzyme in a mammal. The methods generally comprise administering to the mammal a composition comprising a nanoplatform assembly according to any of the embodiments described herein dispersed in a pharmaceutically-acceptable carrier wherein the second particle is characterized as having a detectable signal. The nanoplatform assembly is exposed to an energy source to generate the detectable signal from the second particle by exposing the region of the mammal's body suspected of having the target enzymatic activity. Changes (if any) of the detectable signal are discerned during contact of the nanoplatform with the enzyme in the body, wherein these changes correspond to the active enzyme activity in the sample.

DETAILED DESCRIPTION

Figure 1:
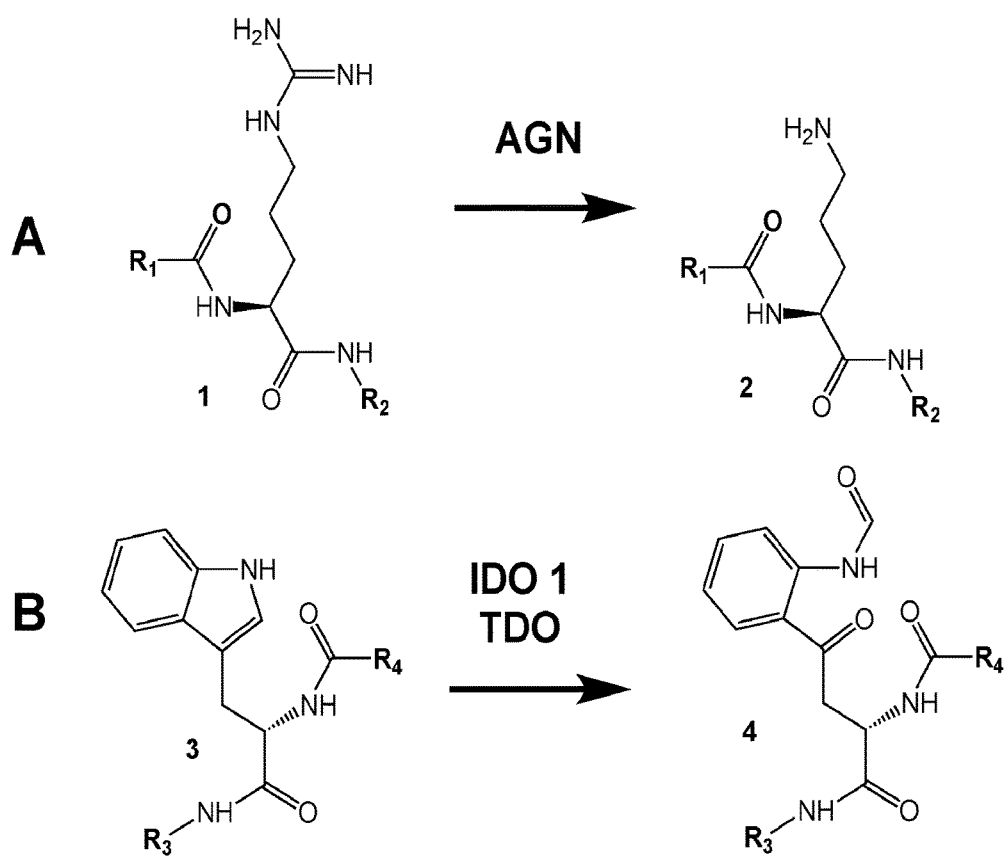
FIG. 1 depicts the reaction mechanism for posttranslational modification of (A) arginine to ornithine; and (B) tryptophan to N-formyl-kynurenine, where R1-R4 designate the rest of the peptide chain.

The present invention is concerned with nanoplatforms and assays for enzyme detection based upon posttranslational modification of enzyme substrates (i.e., peptide sequences) without enzymatic cleavage. In use, the oligopeptide tether between a central carrier particle and a detectable particle is modified by the target enzyme. For instance, as illustrated in FIG. 1, (A) arginine (1) is transformed into ornithine (2) by arginase I and II (AGN), and (B) tryptophan (3) is transformed into N-formyl-kynurenine (NFK) (4) by both, indoleamine 2,3-dioxygenase (IDO1) and tryptophan 2,3-dioxygenase (TDO). All three enzymes are able to react with their amino acid substrate sequences when part of an oligopeptide, which enables the design of posttranslational nanoplatforms.

Arginase, indoleamine 2,3-dioxygenase and tryptophan 2,3-dioxygenase are biomarkers for immune-suppression. Local and systemic immune suppression occurs after Surgical Trauma, and is a hallmark of numerous cancers, as well as Pelvic Inflammatory Disease (PID). In veterinary medicine, immune suppression is typical in subclinical and clinical metritis and mastitis.

Figure 2:
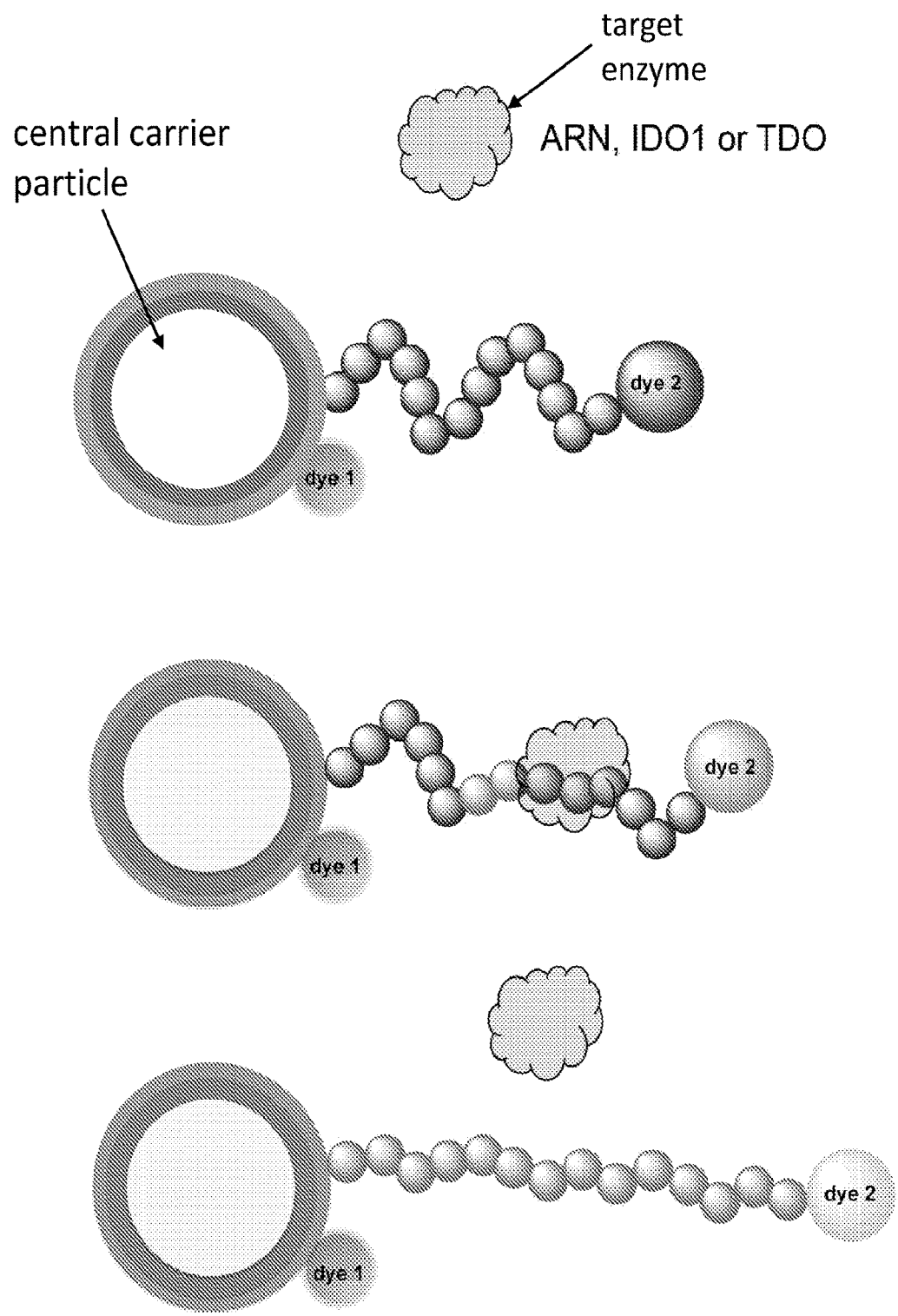
FIG. 2 is a cartoon illustration of the posttranslational modification mechanism of the nanoplatform assemblies using two particles/dyes and a central carrier particle.

Whereas nanoplatforms for protease detection, such as those described in U.S. Pat. No. 8,969,027, incorporated by reference herein to the extent not inconsistent with the present disclosure, feature "protease consensus sequences" that undergo enzymatic cleavage, posttranslational modification does not cut/sever the oligopeptide between the nanoparticle and dye, but changes the chemical characteristics of the amino acid side chains. That leads to changed motion characteristics, which, in turn, leads to a change in the average distance between two particles, resulting in a characteristic change in a detectable signal for the particles used in the nanoplatform, such as a fluorescence spectrum. The observable change in fluorescence (increase or decrease, depending on the chemical nature of the peptide sequences before and after posttranslational modification) is a function of enzyme concentration. The quenching effect can be enhanced by tethering a second dye to the surface of the nanoparticle to facilitate FRET (Förster Resonance Energy Transfer). The general mechanism is depicted via a cartoon illustration in FIG. 2.

The nanoplatforms for arginase, indoleamine 2,3-dioxygenase, and tryptophan 2,3-dioxygenase detection are able to detect the enzymatic activity of the target enzymes directly. Most other methods detect the enzymes indirectly via substrate degradation and subsequent measurement of substrate concentration. This is of importance, because other enzymes e.g., NO-Synthase use the same substrates, but have different physiological functions.

The diagnostic assays of the invention comprise a nanoplatform assembly. The nanoplatform assembly is comprised of an oligopeptide, which is used as a peptide linkage between two particles. More preferably, the linker is comprised of an oligopeptide containing a substrate sequence for the target enzyme (i.e., a sequence for a substrate that is "modifiable" by the enzyme, meaning that the substrate sequence is chemically or physically transformed by the target enzyme, but not cleaved). The nanoplatforms comprise a central carrier particle to which a first particle and a second particle are attached. In one or more embodiments, the first particle is directly tethered or attached to the central carrier particle, such as through an amide bond. In other words, the phrase "directly attached" as used herein means that the first particle is connected directly to the surface of the central particle, or to a ligand layer on the surface of the central particle (and is not attached via an enzymatic substrate sequence). In one or more embodiments, the second particle is attached to the central carrier particle via the oligopeptide substrate sequence. In other words, the central carrier particle is attached to one end (C-terminus) of the oligopeptide sequence and the second particle is attached to the other end (N-terminus) of the oligopeptide sequence.

In the initial nanoplatform assembly, the oligopeptide has a folded secondary structure, such as an alpha-helix and/or beta-sheet structure, so that the second particle is separated from the central carrier particle (and directly attached first particle at the carrier particle's surface) by a first distance. In the presence of the target enzyme, the enzyme modifies the oligopeptide sequence (without cleavage), and more particularly modifies both the primary structure (amino acid residues and metabolic products) and the secondary structure of the oligopeptide sequence. Such "modification" or "posttranslational modification" as used herein, refers to conversion or transformation of the amino acid residues (and particularly the side chains) in the substrate sequence to a different form and/or different residue. This, in turn, extends, "unfolds," or "unravels" the secondary structure and/or increases and/or decreases the mobility of the oligopeptide sequence, and thus changes the distance of the second particle to the central carrier particle (and directly attached first particle). Accordingly, after being exposed to the target enzyme, the second particle is then separated from the central carrier particle (and directly attached first particle) by a second distance that is now different (closer or farther) from the first distance in the initial nanoplatform. The first and/or second particles generate a detectable signal, and such changes in the signal due to the modification of the oligopeptide chain can be detected and correlated with enzymatic activity of the target enzyme.

The central carrier particle can be a variety of particles discussed herein, with the proviso that it can be attached with two or more different particles. Preferably, the nanoplatforms comprise a plurality of the first particle attached to a single central carrier particle, and a plurality of the second particle attached to the same carrier particle. Preferably, the amount of first particles attached to the carrier particle is greater than the amount of second particles tethered to the carrier particle. In one or more embodiments, the ratio of the number of first particles (directly attached) to second particles (tethered) on each carrier particle is from about 1:1 to about 1:100, more preferably from about 1:1.5 to about 1:35, and more preferably about 1:35. In one or more embodiments, the central carrier particle is one that is capable of SET (Dipole-surface Energy Transfer), and/or participates in quenching of the detectable signal of one or both of the attached particles (and particularly the second particle). In one or more embodiments, the central carrier particle does not actively participate in the signal being detected in the assay, but is simply a carrier structure for tethering the first and second particles. Non-plasmonic particles can be used in certain embodiments.

The first and second particles are particles that have a detectable signal, such as fluorescence or color change, which can be perceived visually or measured with an appropriate instrument. In one or more embodiments, the first and second particles are selected to show intense FRET in the pair. In one or more embodiments, the first and second particles are paired so as to enhance the SET quenching of the carrier particle.

The nanoplatforms are particularly suitable for detection methods based upon surface plasmon resonance and FRET between non-identical particles (i.e., nanoparticles or a dye and porphyrin, or two different dyes). FRET describes energy transfer between two particles. Surface plasmon resonance is used to excite the particles. A donor particle initially in its excited state, may transfer this energy to an acceptor particle in close proximity through nonradiative dipole-dipole coupling. Briefly, while the second particle is bound by the oligopeptide in its initial state, a first emission is observed upon excitation of the donor particle. Once the enzyme modifies the linkage, FRET change is observed, and the emission spectra changes. In some instances, only the donor emission is observed. In other instances, the emission spectra simply changes (increases or decreases). In more detail, if both particles are within the so-called Förster-distance, energy transfer occurs between the two particles and a red-shift in emission is observed. During this ultrafast process, the energy of the electronically excited state or surface plasmon of the second particle is at least partially transferred to the first particle. In some embodiments, this means that a detectable signal (e.g., fluorescence, light) is emitted from the first particle. However, once the distance between the two particles is changed by the enzyme, light is emitted only from the second particle and a distinct blue-shift in absorption and emission can be observed. This is because the distance between both particles increases. In other embodiments, a signal may be detectable from both particles in the initial nanoplatform, however, upon modification of the substrate sequence, the signal intensity from the second particle increases as the distance between the first and second particles increases.

In one or more embodiments, the first particle (directly attached to the central particle) is an acceptor and the second particle (tethered via the oligopeptide) is a donor. In general, excitation of the nanoplatform is directed towards the particle having a higher energy state (e.g., the donor particle). Excitation of the second particle can preferably performed between about 400 nm and about 1500 nm, more preferably between about 500 nm to about 800 nm, and even more preferably between about 650 nm and about 800 nm. When using chromophore/luminophore particle pairs, there is also preferably an overlap between the excitation spectrum of the first chromophore/luminophore and the fluorescence or phosphorescence spectrum of the second chromophore/luminophore to permit adequate Förster energy transfer. In one embodiment, cyanine 5.5 (donor) and cyanine 7.0 (acceptor) form a very attractive FRET-pair.

In the assay, so-called Förster-distance, energy transfer occurs between the first and second particles and a change in absorbance and/or emission of the nanoplatform is observed. During this ultrafast process, the energy of the electronically excited state or surface plasmon of the second particle is at least partially transferred to the first particle. Excitation is preferably performed with an energy source of appropriate wavelength selected from the group consisting of a tungsten lamp, laser diode, laser, and bioluminescence (e.g., luciferase, renilla, green fluorescent protein). The changes in absorption and/or emission of the particles as the enzyme in the sample modifies (without cleaving) the oligopeptide linkers will be observed over a time period of from about 1 second to about 120 minutes, preferably from about 1 second to about 30 minutes, and in some cases from about 30 seconds to about 10 minutes (when in the presence of an aggressive tumor or high enzyme concentration).

In practice, the assay can first be calibrated for the particular nanoplatform using a control sample with and without the target enzyme, as described in the working examples.

One advantage of the inventive nanoplatforms is the flexibility to adapt the nanoplatform structure and assays by modifying the particles, oligopeptide linkages, and the like to suit the sensor technology available, and likewise, using a variety of sensor technologies for detecting enzyme activity associated with various conditions.

The nanoplatforms may be used to detect enzymatic activity in a fluid sample comprising a biological fluid, such as urine or blood (serum) samples of a mammal. In one aspect, a urine sample is collected from the mammal and physically mixed with the nanoplatform assembly. The nanoplatform can then be excited using the appropriate energy source. The wavelength used will depend upon the particles used in the nanoplatform assembly. The changes in absorption and emission of the particles as the enzyme, if present, in the urine sample modifies (without cleaving) the oligopeptide linkers will be observed over a time period. In some embodiments, the presence of the enzyme is indicated by an absorption and emission blue-shift of between about 5 and about 200 nm. Blood (serum) can also be collected from the mammal and analyzed like urine discussed above.

In an alternative embodiment, nanoplatforms may be used to detect enzymatic activity in vivo in a mammal. The nanoplatform assembly, or composition comprising the nanoplatform assembly, is preferably administered using a pharmaceutically-acceptable carrier. The nanoplatform assembly can be administered by injection into the bloodstream. Alternatively, the nanoplatform assembly can be administered by injection to a localized region, such as directly into or near the tumor site, or other region of interest in the mammal's body. Liposomes, hollow vesicles or other suitable delivery platforms in which the nanoplatform can be dispersed can be used to transport the nanoplatform to the appropriate region of interest in the mammal's body. As with in vitro detection, the nanoplatform can then be excited using the appropriate energy source. The wavelength used will depend upon the particles used in the nanoplatform assembly. In one or more embodiments, one or two intersecting Ti:sapphire lasers are used to excite the nanoplatform. Other suitable excitation sources include Nd:YAG-lasers (first harmonic at 1064 nm), and any kind of dye-laser, powered by the second harmonic of the Nd:YAG-laser at 532 nm. The changes in absorption and emission of the particles as the enzyme, if present, in the body modifies (without cleaving) the oligopeptide linkers will be observed over a time period. The spectra from the particle(s) in the nanoplatform can be analyzed using an appropriate sensing instrument, and may also be visually discernable using a camera, microscope, or confocal microscope. The spectra from the target region will have a different color or spectra than the healthy tissue regions due to the higher activity of the target enzymes in the target regions (i.e., tumor region, etc.).

Using either sensor method (in vitro or in vivo), the assay time of the present invention is dependent upon the concentration of enzyme present in the sample or tissue. Posttranslational modification speeds will increase by several times per order of magnitude of increase in enzyme concentration. For example, in the presence of an aggressive tumor, assay time can be as fast as minutes or sections. In healthy tissue, it can take hours for activity to be detected. Thus, the faster the assay, the more aggressive the tumor, and the greater the likelihood of metastatic potential of the tumor. Likewise, enzyme activity can also be used to detect regions of inflammation and inflammation-associated immune-suppression, with higher concentrations of enzymatic activity being correlated to increased inflammatory responses in the tissue.

As mentioned, the nanoplatforms can be used to detect arginase, and particularly arginase II. Arginine is an exemplary substrate for use in detecting arginase activity. Thus, substrate sequences for arginase detection will include, inter alia, a plurality of arginine residues. Arginine (R) reacts to ornithine (O) in the presence of arginase II. This chemical transformation occurs without proteolytic cleavage of the oligopeptide.

The nanoplatforms can also be used to detect indoleamine 2,3-dioxygenase 1 and/or tryptophan 2,3-dioxygenase. Exemplary IDO1 substrates include L-tryptophan, D-tryptophan, 5-hydroxy-tryptophan, tryptamine, and serotonin. TDO is, however, specific for L-tryptophan. Thus, substrate sequences for IDO1 detection would include, for example, a plurality of residues of tryptophan, while substrate sequences for TDO would include specifically L-tryptophan residues. Despite catalyzing the same reaction, the two enzymes have little structural similarity. Therefore, if necessary, either one can be inhibited while retaining the activity of the other.

When measuring IDO1 and TDO concentrations in a sample, the same nanoplatform can be utilized, together with either an IDO1 inhibitor (e.g. 1-Methyl-D-tryptophan) or a TDO inhibitor (e.g. 680C91), which permits differentiation between both enzymes even when using the same nanoplatform (e.g., one containing L-tryptophan substrate sequence).

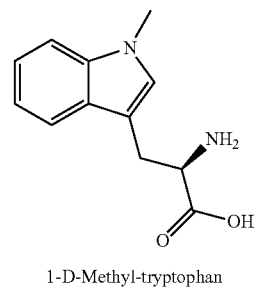

1-D-Methyl-tryptophan

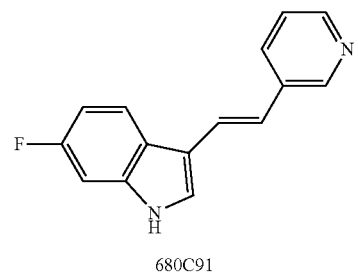

680C91

The assays can be run in the presence of inhibitors to achieve selectivity over proteases potentially present in the sample. In other words, it will be appreciated that biological samples tested using the inventive nanoplatforms may contain proteases, which can interfere with the detection of AGN, IDO1, or TDO. That is, the proteases can cleave the oligopeptides instead of simply modifying the side chains. Thus, in one or more embodiments, the assays can be performed in the presence of one or more protease inhibitors (i.e., protease inhibitor(s) can be added to the sample, along with the nanoplatform). An exemplary protease inhibitor is known as Ilomastat.

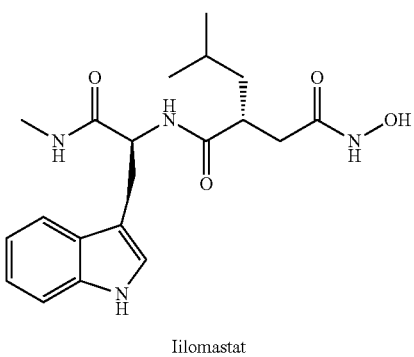 [SMILES: CNC(=O)[C@H](Cc1c[nH]c2ccccc12)NC(=O)[C@@H](CC(=O)NO)CC(C)C]

Iilomastat

Oligopeptide Linker

The following oligopeptides can be utilized for the various embodiments of the invention. Exemplary oligopeptides are preferably less than 55 residues in length, and in some embodiments are less than 30 residues in length, more preferably less than 25 residues in length, and even more preferably less than 15 residues in length.

1) Arginase (AGN) substrate sequences comprise (consist essentially or even consist of) sequences according to (I) and/or (II):

$$(X)_n(R)_m(X)_l \quad \text{(SEQ ID NO:1)}, \quad \text{(I)}$$

where:
each R: arginine;
each X: any amino acid, preferentially G or C;
m: 3-10;
n: 1-6; and
l: 1-6; or $$(X)_n(RJ)_m(X)_l \quad \text{(SEQ ID NO:2)}, \quad \text{(II)}$$

where:
each R: arginine;
each X: any amino acid, preferentially G or C;
each J: any amino acid capable of supporting alpha helices: E, A, L, M, K, R, Q, or H;
m: 2-20;
n: 1-6; and
l: 1-6.

The transformation of arginine into ornithine proceeds stepwise and most likely in a random pattern. It ends when all arginine residues in the substrate sequence have been transformed into orthinine residues.

2) Indoleamine 2,3-dioxygenase 1 (IDOL) and Tryptophan 2,3-dioxygenase (TDO) substrate sequences comprise (consist essentially or even consist of) sequences according to (III) and/or (IV):

$$(X)_n(W)_m(X)_l \quad \text{(SEQ ID NO:3)}, \quad \text{(III)}$$

where:
each W: L-tryptophan for TDO, L- or D-tryptophan for IDO1;
each X: any amino acid, preferentially G or C;
m: 3-10
n: 1-6; and
l: 1-6; or $$(X)_n(WU)_m(X)_l \quad \text{(SEQ ID NO:4)}, \quad \text{(IV)}$$

where:
each W: L-tryptophan for TDO, L- or D-tryptophan for IDO1;
each X: any amino acid, preferentially G or C;
each U: any amino acid capable of supporting beta sheets: G, N, D, P, or S;
m: 2-20;
n: 1-6; and
l: 1-6.

Notably, although other techniques like ELISA (immunoprecipitation assays) is able to detect the enzymes directly, ELISA is not able to differentiate between active enzymes and zymogens (inactive precursors). By using substrates upon which the enzymes must be active, the present assays can directly detect the presence of enzyme activity in a sample. In one or more embodiments, the oligopeptide can also comprise a thiol group at the C-terminus, and a carboxylic acid group at the N-terminus. In some embodiments, the oligopeptide linker comprises a hydrophilic region of at least 10 amino acids N-terminal to the substrate sequence, and a linking region C-terminal to the cleavage sequence, wherein the C-terminal linking region comprises a thiol reactive group at its terminus.

Particles for Assay

A number of different types of particles can be used to form the nanoplatform assemblies for use in the inventive assays, depending upon the type of sensor used to measure the enzyme activity, as discussed in more detail below. Preferably, the excitation and emission spectral maxima of the particles are between 650 and 800 nm. Preferred particles for use in the nanoplatforms are selected from the group consisting of nanoparticles, chromophores/luminophores, quantum dots, viologens, and combinations thereof.

1. Nanoparticles

The term "nanoparticle" as used herein refers to nanocrystalline particles that can optionally be surrounded by a metal and/or nonmetal nanolayer shell. Such nanoparticles can be metal nanoparticles: metal, metal alloy, metal oxide, or core/shell metal nanoparticles (e.g. $Fe_2O_3$, $Fe_3O_4$). Nanoparticles can also be non-metal: non-metal oxide (e.g. $SiO_2$), polysilicone, polysilazane, or polysiloxazane, starburst dendrimers, or polymer latex nanoparticles. Suitable nanoparticles preferably have a diameter of from about 1 nm to about 100 nm, more preferably from about 10 nm to about 50 nm, and even more preferably from about 5 nm to about 20 nm.

Metal nanoparticles can comprise any type of metal (including elemental metal) or metal alloy. Preferably, the metal or metal alloy nanoparticles comprise a metal selected from the group consisting of gold (Au), silver (Ag), copper (Cu), nickel (Ni), palladium (Pd), platinum (Pt), cobalt (Co), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., FeO, $Fe_3O_4$, $Fe_2O_3$, $Fe_xO_y$ (non-stoichiometric iron oxide), CuO, NiO, $Ag_2O$, $Mn_2O_3$), hydroxides, sulfides, selenides, and tellurides of the foregoing, and combinations thereof.

In some embodiments, metal nanoparticles will be bimagnetic and comprise a metal or metal alloy core and a metal shell. Core/shell metal nanoparticles preferably comprise a metal or metal alloy core and a metal shell. Preferred cores are selected from the group consisting of Au, Ag, Cu, Co, Fe, and Pt. Even more preferably, the metal nanoparticles feature a strongly paramagnetic Fe core. Preferred shells are selected from the group consisting of Au, Ag, Cu, Co, Fe, Pt, the metal oxides (e.g., FeO, $Fe_3O_4$, $Fe_2O_3$, $Fe_xO_y$ (non-stoichiometric iron oxide), CuO, $Cu_2O$, NiO, $Ag_2O$, $Mn_2O_3$)

thereof, and combinations thereof. Particularly preferred metal core/shell combinations are selected from the group consisting of Fe/Au, Fe(0)/Fe$_3$O$_4$, and Au/Fe$_2$O$_3$. A particularly preferred metal nanoparticle is a superparamagnetic Fe/Fe$_3$O$_4$ core shell nanoparticle. The core of the metal nanoparticle preferably has a diameter of from about 2 nm to about 100 nm, more preferably from about 3 nm to about 18 nm and more preferably from about 5 nm to about 9 nm. The metal shell of the core/shell nanoparticle preferably has a thickness of from about 1 nm to about 10 nm, and more preferably from about 1 nm to about 2 nm.

The nanoparticles preferably have a Brunauer-Emmett-Teller (BET) multipoint surface area of from about 20 m$^2$/g to about 500 m$^2$/g, more preferably from about 50 m$^2$/g to about 350 m$^2$/g, and even more preferably from about 60 m$^2$/g to about 80 m$^2$/g. The nanoparticles preferably have a Barret-Joyner-Halenda (BJH) adsorption cumulative surface area of pores having a width between 17.000 Å and 3000.000 Å of from about 20 m$^2$/g to about 500 m$^2$/g, and more preferably from about 50 m$^2$/g to about 150 m$^2$/g. The nanoparticles also preferably have a BJH desorption cumulative surface area of pores having a width between 17.000 Å and 3000.000 Å of from about 50 m$^2$/g to about 500 m$^2$/g, and more preferably from about 50 m$^2$/g to about 150 m$^2$/g. The nanoparticle population is preferably substantially monodisperse, with a very narrow size/mass size distribution. More preferably, the nanoparticle population has a polydispersity index of from about 1.2 to about 1.05. It is particularly preferred that the nanoparticles used in the inventive nanoplatforms are discrete particles. That is, clustering of nanocrystals (i.e., nanocrystalline particles) is preferably avoided.

The nanoparticles can be stabilized or non-stabilized. Stabilized nanoparticles preferably comprise an organic monolayer surrounding the nanoparticle core. The term "stabilized" as used herein means the use of a ligand shell or monolayer to coat, protect (e.g., from bio-corrosion), or impart properties (e.g., water solubility) to, the nanoparticle. The monolayer can be comprised of several of the same ligands (i.e., homoligand) or of mixed ligands. Various techniques for attaching ligands to the surface of various nanoparticles are known in the art. For example, nanoparticles may be mixed in a solution containing the ligands to promote the coating of the nanoparticle. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. The number of ligands required to form a monolayer will be dependent upon the size of the nanoparticle.

The ligands comprise functional groups that are attracted to the nanoparticle's metal surface. Preferably, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. Preferred organic monolayers are selected from the group consisting of alkanethiolate monolayers, aminoalkylthiolate monolayers, alkylthiolsulfate monolayers, and organic phenols (e.g., dopamine and derivatives thereof). The thickness of the organic monolayer is preferably less than about 10 nm, and more preferably less than about 5 nm. Particularly preferred stabilized nanoparticles are selected from the group consisting of trioctyl-phosphinoxide-stablized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

For attachment to the oligopeptide linkages, the preferred ligands will preferably readily react with the thiol group of the terminal cysteine of the oligopeptide linkage. The nanoparticle surface will preferably be essentially completely covered with ligands. That is, at least about 70%, preferably at least about 90%, and more preferably about 100% of the surface of the nanoparticle will have attached ligands. The number of ligands required to form a monolayer will be dependent upon the size of the nanoparticle (and monolayer), and can be calculated using molecular modeling or ligand modeling methods.

Various techniques for attaching ligands to the surface of various nanoparticles are known in the art. For example, nanoparticles may be mixed in a solution containing the ligands to promote the coating of the nanoparticle surface. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding.

2. Chromophores/Luminophores

Chromophore/luminophore particles suitable for use in the inventive assays include any organic or inorganic dyes, fluorophores, phosphophores, light absorbing nanoparticles (e.g., Au, Ag, Pt, Pd), combinations thereof, or the metalated complexes thereof. Preferably, the chromophore/luminophore particles have a size (maximum surface-to-surface dimension, i.e., diameter) of less than about 100 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, cyanines (Cy7, Cy7.5, Cy5.0, Cy5.5, Cy3Cy5 ET, Cy3B, Cy3.0, Cy3.5, Cy2), CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Cyanine dyes are particularly preferred organic dyes for use in the nanoplatforms. The fluorescent cyanine dye is tethered to the nanoparticle and experiences rapid fluorescence quenching by the plasmon of the Fe(0)-core. This is observed as long as the tether is smaller than the Förster-radius of the cyanine dye (5-6 nm for Cy3.0 and Cy3.5, 6-7 nm for Cy5.0 and Cy5.5, and approx. 7 nm for Cy7 and Cy7.5). The maximal length of the tether, consisting of the ligand (~2.84 nm) and not more than 12 amino acid residues in the cleavage sequences (up to 4 nm) indicates that shorter cleavage sequences (uPA and MMP's) are suitable for use with Cy3.x and Cy5.x dyes, whereas the cathepsins are preferably linked to Cy5.x and Cy.7.x dyes to permit optimal quenching of the tethered cyanine dyes. For all of the cyanines, their emission maxima are red-shifted with respect to the autofluorescence of human urine. Multiple cyanines can be linked to a single nanoparticle to create oligoplexing nanoplatforms, to measure the activity of up to four enzymes simultaneously. All four dyes in the UVA or blue region of the electromagnetic spectrum can be excited simultaneously, or each dye can be excited individually. All cyanine dyes have an excitation maximum, which is blueshifted by 20-25 nm with respect to their emission maximum (typical for fluorescent singlet states). Exemplary emission spectra of: NS-Cy3.0 ($\lambda$ex=538, $\lambda$em=560), NS-Cy5.5 ($\lambda$ex=639, $\lambda$em=660), NS-Cy7.0 ($\lambda$ex=740, $\lambda$em=760) and NS-Cy7.5 ($\lambda$ex=808, $\lambda$em=830).

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

3. Quantum Dots

A quantum dot is a semiconductor composed of atoms from groups II-VI or III-V elements of the periodic table (e.g., CdSe, CdTe, InP). The optical properties of quantum dots can be manipulated by synthesizing a (usually stabilizing) shell. Such quantum dots are known as core-shell quantum dots (e.g., CdSe/ZnS, InP/ZnS, InP/CdSe). Quantum dots of the same material, but with different sizes, can emit light of different colors. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Quantum dots feature slightly lower luminescence quantum yields than traditional organic fluorophores but they have much larger absorption cross-sections and very low rates of photobleaching. Molar extinction coefficients of quantum dots are about $10^5$-$10^6$ $M^{-1}$ $cm^{-1}$, which is 10-100 times larger than dyes.

Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (e.g. CdSe/ZnS) has a higher energy conduction band and a lower energy valance band than that of the core, resulting in confinement of both electron and hole in the core. The conduction and valance bands of the shell of type II quantum dots (e.g., CdTe/CdSe, CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are most preferred. The alloy composition and internal structure, which can be varied, permits tuning the optical properties without changing the particles' size. These quantum dots can be used to develop near infrared fluorescent probes for in vivo biological assays as they can emit up to 850 nm.

Particularly preferred quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe). The quantum dots are preferably small enough to be discharged via the renal pathway when used in vivo. More preferably, the quantum dots are less than about 10 nm in diameter, even more preferably from about 2 nm to about 5.5 nm in diameter, and most preferably from about 1.5 nm to about 4.5 nm in diameter. If different color emission is needed for creating multiple sensors (multiplex detection), this can be achieved by changing the size of the quantum dot core yielding different emission wavelengths. The quantum dots can be stabilized or unstabilized as discussed above regarding nanoparticles. Preferred ligands for stabilizing quantum dots are resorcinarenes.

Compositions and Applications

The nanoplatforms can be part of a composition comprising the inventive nanoplatform assembly and a pharmaceutically-acceptable carrier. The term carrier is used herein to refer to diluents, excipients, vehicles, and the like, in which the nanoplatform may be dispersed. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the nanoplatform other agents and to minimize any adverse side effects in the subject (for in vivo administration), as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), or other acceptable vehicles, and the like.

The nanoplatforms for enzyme detection proposed here are, on average, 1,000 times more sensitive than ELISA, 10,000 more sensitive than fluorescence assays and 50,000 more sensitive than colorimetric assays.

The nanoplatforms described here can be used together with our nanoplatforms for protease detection (U.S. Pat. No. 8,969,027) in fluorescence plate readers to detect enzymatic activity in blood serum samples. No other technology to date is able to do that, because the concentrations of virtually all enzymes of interest in blood serum are low (<10-12 M). These measurements will permit the following applications of this technology:

1) Assays for immune depression, which will enable even better cancer detection, including early detection of solid tumors (stage 1), cancer recurrence and monitoring of treatment Success/Failure;
2) Detection of immune complications or immunosuppression after surgical or clinical trauma;
3) Detection of immune weakness after birth (leading to Pelvic Inflammatory Disease);
4) Detection of the efficacy of immune therapy;
5) Detection of Vascular Stiffness, Diabetic Cardiac Disease and especially early developing Cardiac Disease;
6) Detection of Traumatic Brain Injury;
7) Early Detection of Multiple Sclerosis and Atherosclerosis;

8) Early Detection of Retinal Neurovascular Injury and Diabetic Retinopathy;
9) Detection of the efficacy of allergy treatment;
10) Detection of subclinical metritis, mastitis and location of retained placenta in dairy cows;
11) Monitoring of wound healing (and inflammatory processes); and
12) Monitoring liver activity of patients with various liver-associated diseases (e.g., hepatitis C, HIV/AIDS, alcoholism etc.).

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Materials

1. Synthesis of Dopamine-Coated Core/Shell Iron/Iron Oxide (Fe/Fe$_3$O$_4$) Nanoparticles Polycrystalline nanoparticles were synthesized by thermal decomposition of Fe(CO)$_5$ in the presence of oleylamine and hexadecylammonium chloride (HADxHCl) using 1-octadecene (ODE) as solvent. Briefly, a 250 mL, three-necked, round-bottom flask equipped with a magnetic stir bar, one cold water cooled jacket condenser on the middle neck, one septum and one temperature probe on each of the outer necks was charged with 60 mL 1-octadecene (ODE), 0.9 mL oleylamine and 0.831 g hexadecylammonium chloride (HADxHCl). The reaction system was connected to a Schlenk line through the top of the jacket condenser. The reaction mixture was degassed at 120° C. for 30 min with vigorous stirring. After being refilled with argon, the reaction mixture was heated to 180° C. Three portions of 0.7 mL Fe(CO)$_5$ were injected into the reaction mixture via syringe, every 20 min. The reaction mixture was kept at 180° C. for another 20 min after the last injection, and then cooled to room temperature naturally. The supernatant was decanted, and the iron nanoparticles accumulated on the magnetic stir bar were washed with hexane and ethanol. The product was dried in vacuum and stored at room temperature under argon for further use. Based on the iron content of the nanoparticles, which was determined spectrophotometrically after dissolving the nanoparticles in aqueous HCl (1.0 M) and subsequent complexation with ferrozine (sodium 4,4'-(3-(pyridin-2-yl)-1,2,4-triazine-5,6-diyl)dibenzenesulfonate), the yield of the reaction was 95%. Transmission electron microscopy (TEM) indicates, an average Fe(0) core diameter of the Fe/Fe$_3$O$_4$-nanoparticles of 17±0.5 nm and Fe$_3$O$_4$ shell thickness of 3.0±0.5 nm.

Next, the Fe/Fe$_3$O$_4$ nanoparticles (0.50 g) were dispersed in 100 mL chloroform via sonication. With vigorous mechanical stirring, a solution of 0.50 g dopamine-hydrochloride in 50 mL chloroform was added drop-wise to the nanoparticle suspension. The reaction mixture was further stirred at room temperature for 24 hours, and then the dopamine coated nanoparticles were collected by centrifugation. After washing with chloroform 5 times, nanoparticles were dried under vacuum. 0.47 g dopamine-coated Fe/Fe$_3$O$_4$ nanoparticles were collected.

2. Cyanine 5.5, 7.0, 7.5 and TCPP Dyes Used in Methods

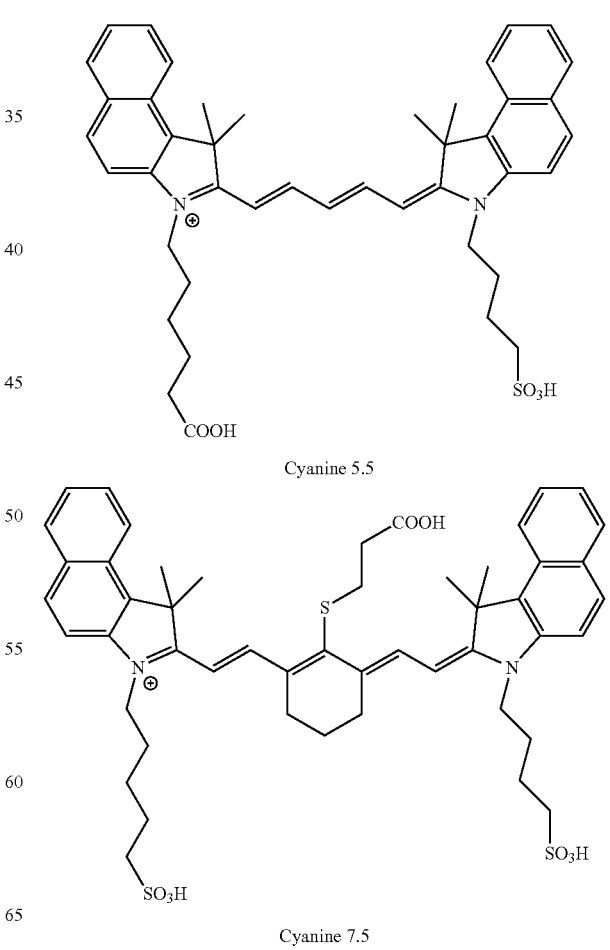

Cyanine 5.5

Cyanine 7.5

-continued

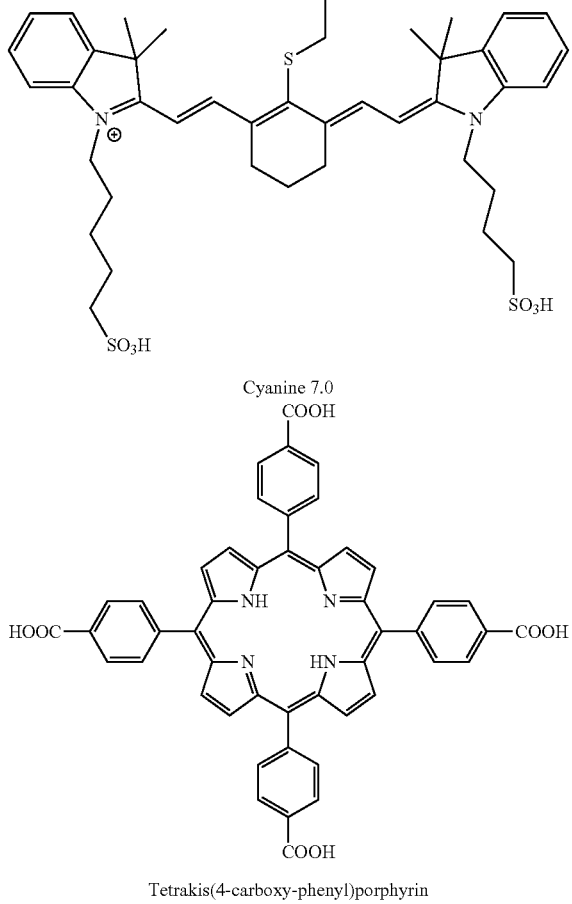

Cyanine 7.0

Tetrakis(4-carboxy-phenyl)porphyrin

3. Peptide Synthesis

GRRRRRRRG (SEQ ID NO:5, "GR$_7$G") and GOOOOOOOG (SEQ ID NO:6, "GO$_7$G") substrate sequences were synthesized by standard solid phase peptide synthesis. Trityl-resin was used as a matrix polymer solid support. The resin was preloaded into a peptide synthesis tube and swelled in dichloromethane (DCM) for 20 minutes and then filtered. DCM was washed away by five consecutive washings with N,N-dimethylformamide (DMF). A mixture of Fmoc protected amino acid and O-benzotriazole-N,N,N',N'tetramethyl-uronium-hexafluoro-phosphate (HBTU) as coupling agent were added, swirled 30 minutes, and then filtered. This step was repeated once. Excess amino acid and the coupling agent were washed away by five DMF washings. Next, 20% piperidine in DMF was used for N-deprotection. Subsequent amino acid coupling was performed after N-deprotection. Both GR$_7$G (SEQ ID NO:5) and GO$_7$G (SEQ ID NO:6) substrate sequences were synthesized using amino acid-by-amino acid repetitive addition from C-terminus to N-terminus.

To prepare peptide-tethered dyes, the dyes were coupled to the N-terminal on the GR$_7$G (SEQ ID NO:5) or GO$_7$G sequence (SEQ ID NO:6) following same coupling conditions as for amino acid addition. Each dye conjugated to a respective substrate sequence was cleaved from the resin and also the side chain protecting groups were removed using a mixture of TFA, TIPS and water (95:2.5:2.5). The peptide-dye conjugates were precipitated in cold ether and collected by centrifuging at 10000 rpm. After precipitation, several DMF washings were carried out to remove the excess of unreacted dye and other reagents. Three final ether washings were carried out, in order to remove leftover DMF.

Directly attached dyes were attached to the nanoparticle via stable amide bonds through the primary amine functionality of the dopamine coating.

Example 2

Preliminary Nanoplatform Sensors

Figure 3:
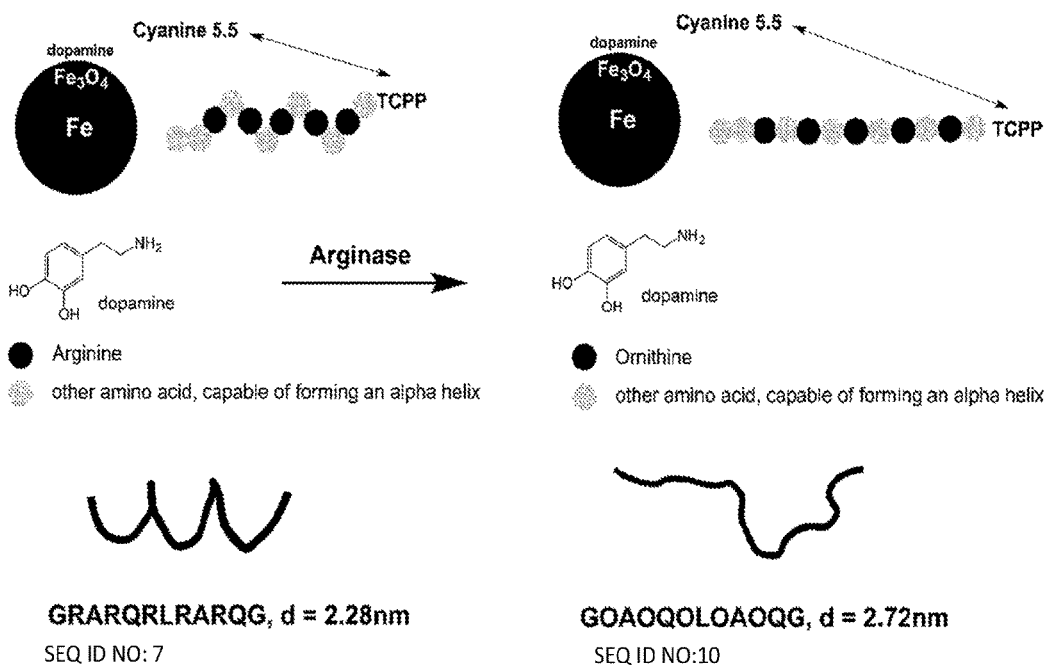
FIG. 3 is a cartoon illustration of an arginase nanoplatform used in Example 2 with cyanine 5.5 and TCPP as the two particles.

In the preliminary work, the nanoplatform sensor design features cyanine dye(s) directly attached to the dopamine ligands on the nanoparticle. Cyanine 5.5 was permanently tethered to the dopamine ligands via amide bonds. Tetrakis (4-carboxy-phenyl)porphyrin (TCPP) was tethered to the nanoparticle via a substrate sequence. The nanoplatforms were incubated with different concentrations of target enzymes in buffer for 60 minutes. See FIG. 3 which is a cartoon illustrating the principles of the nanoplatform, where cyanine 5.5 is dye 1 and TCPP is dye 2, and using the substrate sequence GRARQRLRARQG (SEQ ID NO:7) as the example. The particles are attached via stable amide bonds to the dopamine ligand layer covering the core/shell nanoparticle, with the TCPP being further tethered via the substrate sequence (whereas the cyanine 5.5 is directly attached to the dopamine ligand). In the initial nanoplatform, the substrate sequence has an alpha-helix secondary structure of a first length, such that the distance of the TCPP to the nanoparticle is about 2.28 nm. After incubation with the sample containing arginase II, the arginine residues in the substrate sequence are transformed or converted to orthinine, which results in an extension and unraveling/unfolding of the secondary structure, such that the length of the substrate sequence after this posttranslational modification has increased, and the distance of the TCPP to the nanoparticle is likewise increased to about 2.72 nm. As such, the distance between cyanine 5.5 at the surface of the nanoparticle and the tethered TCPP has also increased. The mechanism is TCPP is a combination of FRET (TCPP donor, cyanine 5.5 acceptor) and SET (plasmonic quenching of cyanine 5.5 (more) and TCPP (less)). Since FRET has an $R^{-6}$ dependence and SET has an $R^{-4}$ dependence, TCPP fluorescence is increased after this conversion.

Figure 4:
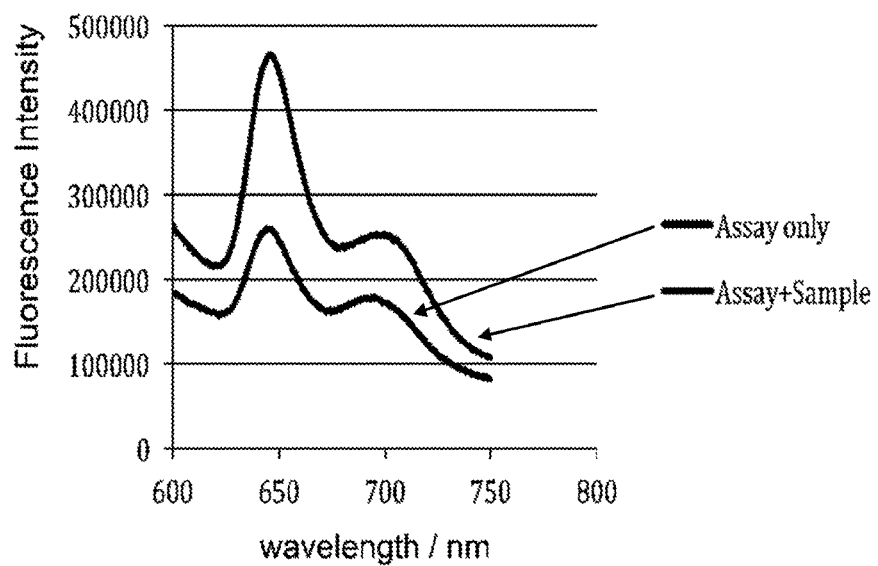
FIG. 4 is the fluorescence spectra of the arginase nanoplatform in Example 2 after 60 min. of incubation with arginase II in PBS.

FIG. 4 shows the fluorescence spectra of the nanoplatform assay before and after 60 min. of incubation with $10^{-10}$ M arginase II in PBS.

Figure 5:
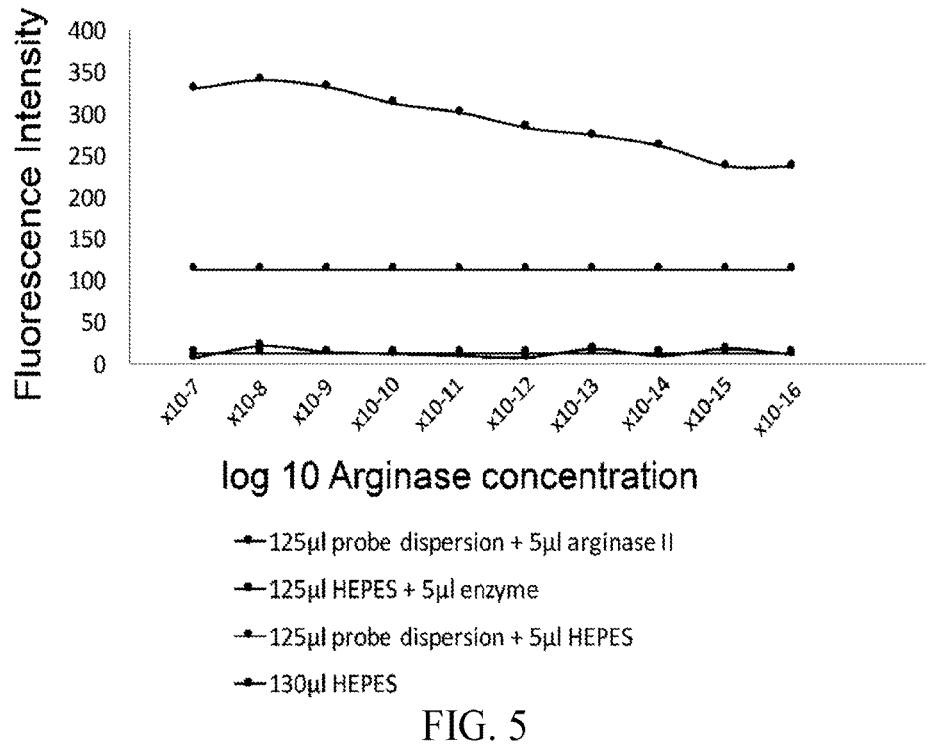
FIG. 5 is a graph of the calibration of the arginase nanoplatform in Example 2 using substrate sequence GRRRRRRRG (SEQ ID NO:5) before and after 60 min. of incubation with arginase II in PBS.

FIG. 5 shows the calibration result of the nanoplatform assay TCPP tethered via oligopeptide sequence GRRRRRRRG (SEQ ID NO:5) before and after 60 min. of incubation with $10^{-9}$ M to $10^{-16}$ M arginase II in PBS. The limit of detection is $10^{-15}$ M arginase II. Above $10^{-8}$M saturation is observed.

Figure 6:
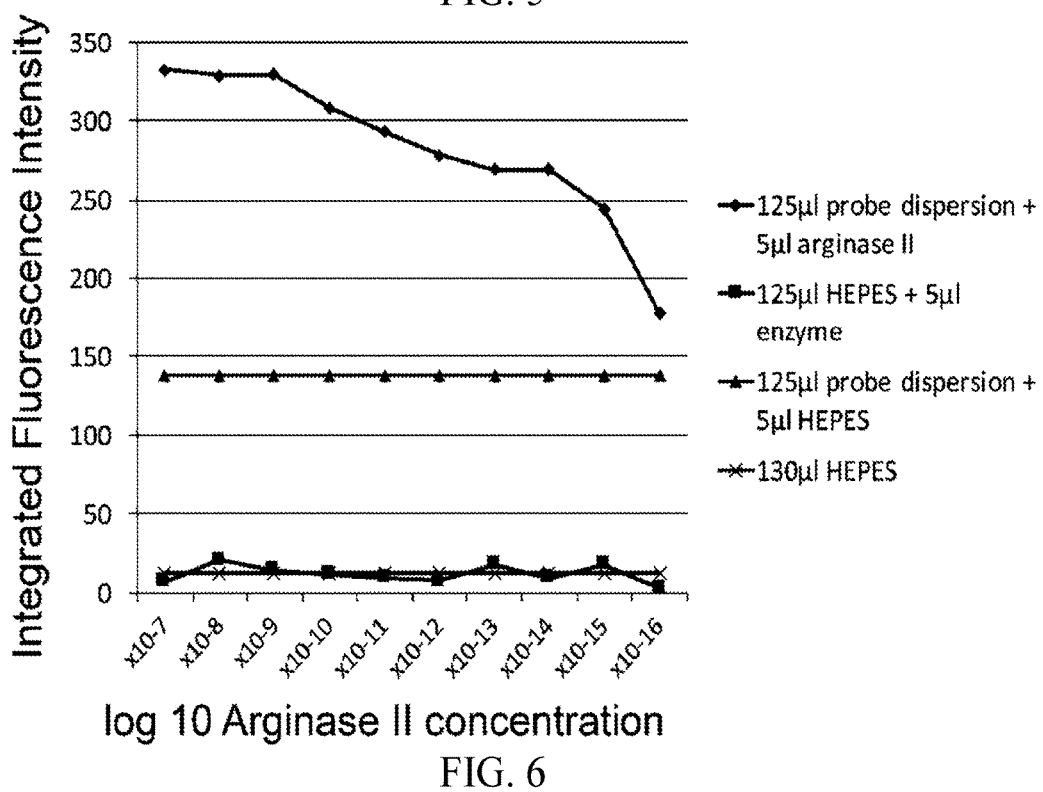
FIG. 6 is a graph of the calibration of the arginase nanoplatform in Example 2 using substrate sequence GRARQRLRARQG (SEQ ID NO:7) before and after 60 min. of incubation with arginase II in HEPES.

FIG. 6 shows the calibration result of the nanoplatform assay TCPP tethered via oligopeptide sequence GRARQRLRARQG (SEQ ID NO:7) before and after 60 min. of incubation with $10^{-7}$ M to $10^{-16}$ M arginase II in HEPES buffer. The limit of detection is estimated to $2\times10^{-16}$M arginase II. Above $10^{-9}$M saturation is observed.

Figure 7:
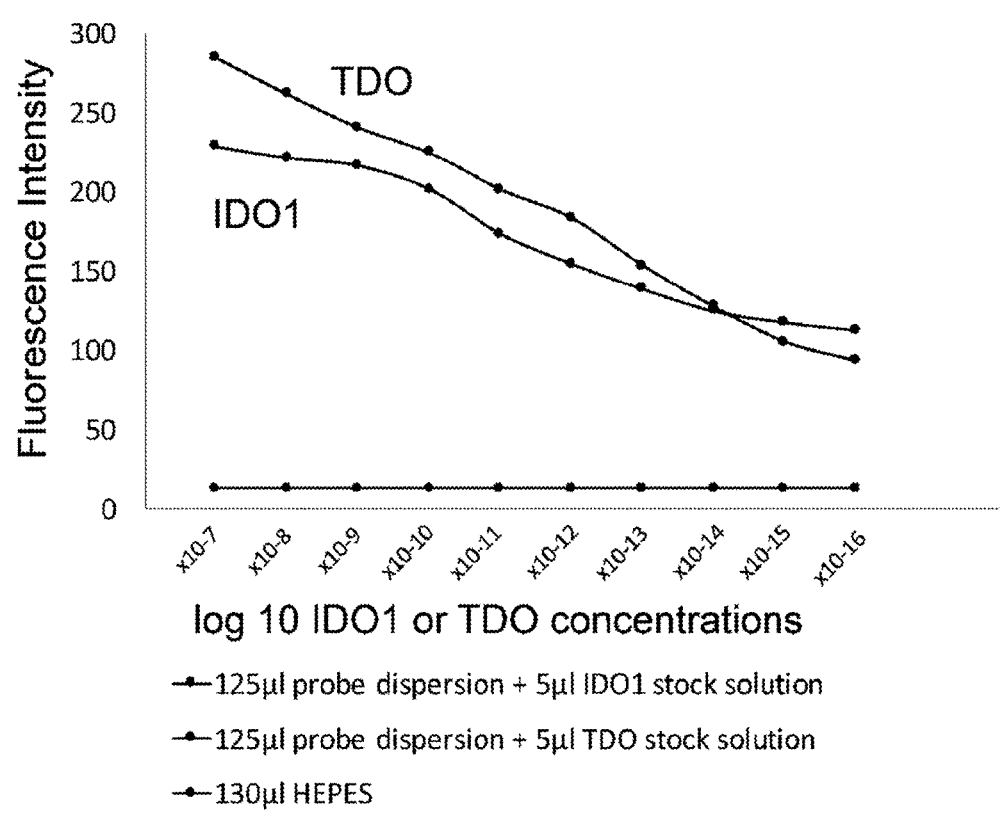
FIG. 7 is a graph of the calibration of the IDO/TDO nanoplatform in Example 2 using substrate sequence GNWPWDWGWDWPWNWG (SEQ ID NO:8) before and after 60 min. of incubation with either IDO1 or TDO in HEPES.

FIG. 7 shows the calibration result of the nanoplatform assay TCPP tethered via oligopeptide sequence GNWPWD-WGWDWPWNWG (SEQ ID NO:8) and directly linked cyanine 5 (dye 1, see Scheme 2) before and after 60 min. of incubation with $10^{-7}$ M to $10^{-16}$ M either IDO1 or TDO (R&D Systems) in HEPES buffer. Whereas the concentration of TDO can be determined over the whole range from $10^{-7}$ to $10^{-16}$ M, the LOD for IDO1 is $10^{-15}$ M. Above $10^{-10}$ M saturation is observed.

Figure 8:
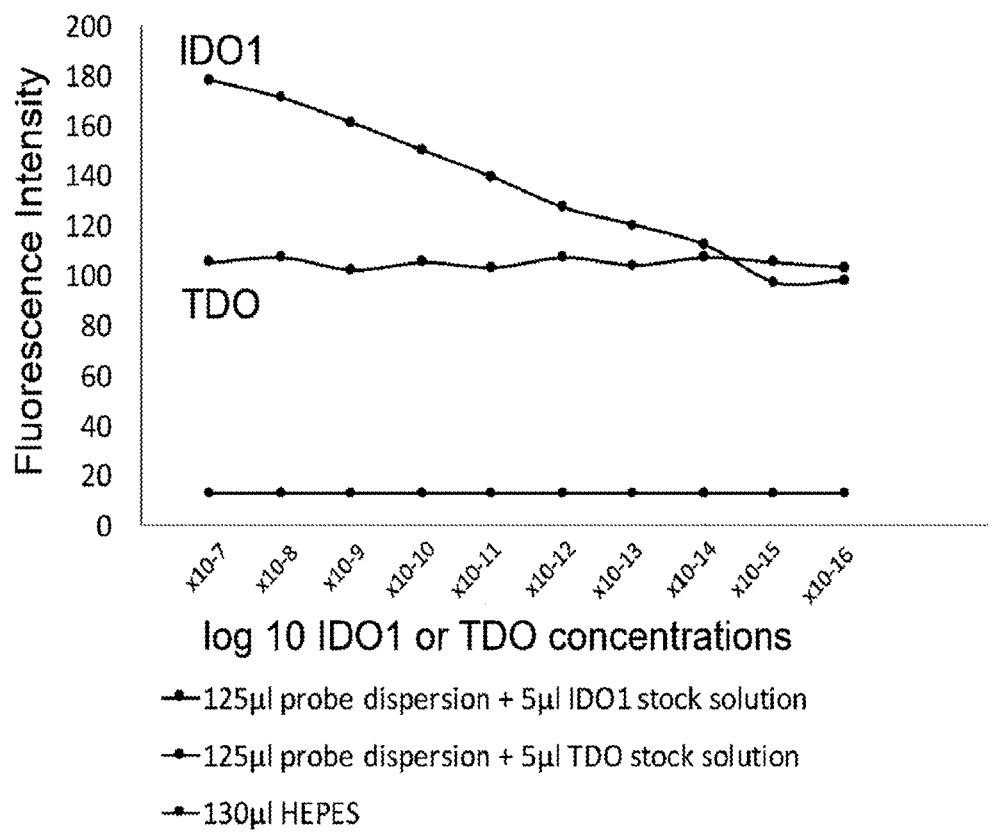
FIG. 8 is a graph of the calibration of the IDO/TDO nanoplatform in Example 2 using substrate sequence GNwPwDwGwDwPwNwG (SEQ ID NO:9) before and after 60 min. of incubation with either IDO1 or TDO in HEPES.

FIG. 8 shows the calibration result of the nanoplatform assay TCPP tethered via oligopeptide sequence GNwPwD-wGwDwPwNwG (SEQ ID NO:9, where lowercase "w" indicates D-tryptophan) before and after 60 min. of incubation with $10^{-7}$ M to $10^{-16}$ M either IDO1 or TDO (R&D Systems) in HEPES buffer. Whereas the concentration of IDO1 can be determined over the range from $10^{-7}$ to $10^{-14}$ M, TDO does not react with the substrate GNwPwDwG-wDwPwNwG (SEQ ID NO:9), because it is specific for L-tryptophan.

Example 3

Arginase Nanoplatform Sensors

Two nanoplatforms for arginase detection were designed and synthesized. Both feature a central dopamine-coated iron/iron oxide nanoparticle to which sulfonated cyanine 7.0 or cyanine 7.5 is tethered via stable amide bonds. In both nanoplatforms, cyanine 5.5 is linked to the N-terminal of the peptide substrate sequence GRRRRRRRG (SEQ ID NO:5). Cyanine 5.5 (donor) and cyanines 7.0/7.5 (acceptors) were used as the FRET-pair. Notably, the fluorescence lifetime of cyanines in water is too short to observe significant plasmonic quenching effects (also known as dipole-surface energy transfer (SET)) between the central $Fe/Fe_3O_4$ nanoparticle and the attached cyanines. This is a design change in comparison with earlier nanoplatforms, in which tetracarboxyphenyl-porphyrin (TCPP), was used as a fluorophore.

1. Sensor 1

125 mg of dopamine coated $Fe/Fe_3O_4$ nanoparticles were dispersed in 2 mL of DMF. A solution of 3 mmol of cyanine 7.0, 3.2 mmol of EDC, 1.7 mmol of DMAP in 1 mL of DMF was added to this dispersion. After sonicating for 1 h, the nanoparticles were precipitated by centrifugation (10,000 RPM for 20 min), and thoroughly washed with DMF (1 mL×10). The number of cyanine 7.0 or 7.5 FRET acceptors per nanoparticle was estimated to 70±5, based on their Vis-absorption spectra. The recovered nanoparticles were redispersed in 2 mL of DMF, and to this dispersion, 2.6 mmol of Cyanine 5.5 linked $GR_7G$ peptide, 3 mmol of EDC, 2.6 mmol of DMAP in 1 mL of DMF was added. After sonicating for 1 h, the nanoparticles were precipitated by a magnet (0.55T), and thoroughly washed with DMF (1 mL×10). After drying in high vacuum, 90-100 mg of nanoplatform was obtained. Cyanine 5.5 (FRET donor) was attached to the N-terminal glycine of $GR_7G$ while the oligopeptide was still bound to the resin, thus eliminating the possibility of unwanted side reactions. Based on UV/Vis spectroscopy, we have estimated that 45±5 cyanine 5.5 dyes were attached to each inorganic nanoparticle via $GR_7G$ tethers.

2. Sensor 2

125 mg of dopamine coated $Fe/Fe_3O_4$ nanoparticles were dispersed in 2 mL of DMF. A solution of 3 mmol of cyanine 7.5, 3.2 mmol of EDC, 1.7 mmol of DMAP in 1 mL of DMF was added to this dispersion. After sonicating for 1 h, the nanoparticles were precipitated by centrifugation (10,000 RPM for 20 min), and thoroughly washed with DMF (1 mL×10). The recovered nanoparticles were redispersed in 2 mL of DMF, and to this dispersion, 2.6 mmol of Cyanine 5.5 linked $GR_7G$ (SEQ ID NO:5) peptide, 3 mmol of EDC, 2.6 mmol of DMAP in 1 mL of DMF was added. After sonicating for 1 h, the nanoparticles were precipitated by a magnet (0.55T), and thoroughly washed with DMF (1 mL×10). After drying in high vacuum, 90-100 mg of nanoplatform was obtained.

Figure 9:
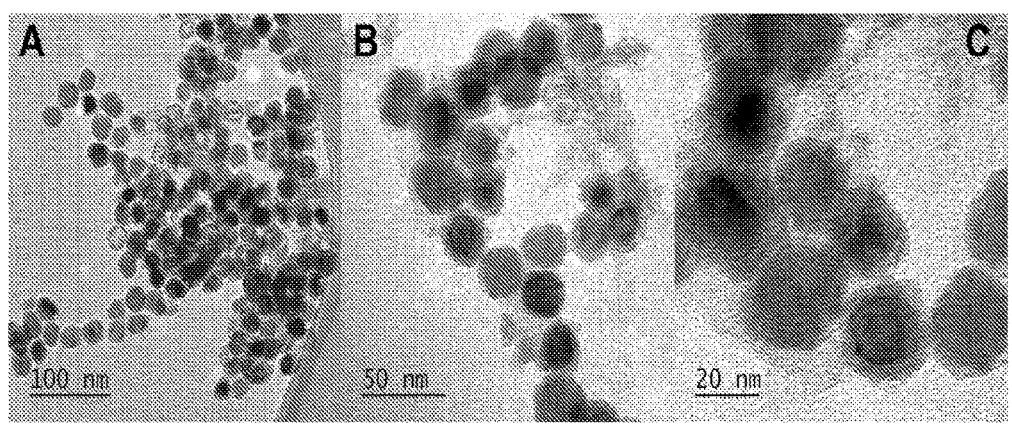
FIG. 9 shows TEM images of nanoparticles and nanoplatforms generated in Example 3: (A) dopamine-coated $Fe/Fe_3O_4$ nanoparticles, (B) dopamine-coated $Fe/Fe_3O_4$ nanoparticles featuring $GR_7G$ (SEQ ID NO:5)-attached cyanine 5.5 and directly attached cyanine 7.5, and (C) dopamine-coated $Fe/Fe_3O_4$ nanoparticles featuring $GR_7G$ (SEQ ID NO:5)-attached cyanine 5.5 and directly attached cyanine 7.0.

TEM images for the nanoplatforms are in FIG. 9 and show the (A) dopamine-coated $Fe/Fe_3O_4$ nanoparticles, (B) dopamine-coated $Fe/Fe_3O_4$ nanoparticles featuring $GR_7G$ (SEQ ID NO:5)-attached cyanine 5.5 and directly attached cyanine 7.5, and (C) dopamine-coated $Fe/Fe_3O_4$ nanoparticles featuring $GR_7G$ (SEQ ID NO:5)-attached cyanine 5.5 and directly attached cyanine 7.0.

3. Calibration

Nanoplatform 1 (FRET pair cyanine 5.5/cyanine 7.0) and nanoplatform 2 (FRET pair cyanine 5.5/cyanine 7.5) were dispersed in PBS (1× phosphate buffered saline) (1 mg/mL). The dispersion was then sonicated for 10 min. 70 µL of this stock solution was added to a series of 30 µL arginase dilutions in 2900 µL of dextran/PBS (10 mg/ml) solution. The concentration ranged from $5.22 \times 10^{-6}$ to $5.22 \times 10^{-13}$ moles of arginase II per liter of 1×PBS. Recombinant Arginase II was purchased from Sigma/Aldrich. After adding the nanoplatform for arginase detection, the dispersion was incubated at 37° C. for 1 h. The resulting fluorescence was then measured using a Fluoromax 2 spectrofluorometer at 25° C., excitation wavelength 680 nm.

Upon excitation at 680 nm, cyanine 5.5 reaches its excited singlet state, which spectrally overlaps with the absorption spectra of both, cyanine 7.0 and cyanine 7.5. The Förster radii for cyanine dyes are ranging from 5 and 8 nm. The maximal length of both oligopeptides $GR_7G$ (SEQ ID NO:5) and $GO_7G$ (SEQ ID NO:6) is 3.2 nm. Considering the principal geometry of the nanoplatform, cyanine 5.5 can easily undergo FRET with both, cyanine 7.0 and cyanine 7.5, because it is within the Förster radius of more than one FRET-acceptor. Since FRET processes feature an $r^{-6}$ dependence of the distance between donor and acceptor, changes in tether mobility will directly either decrease or increase the FRET efficiency. The chemical transformation from arginine to ornithine is causing exactly this effect.

Figure 10:
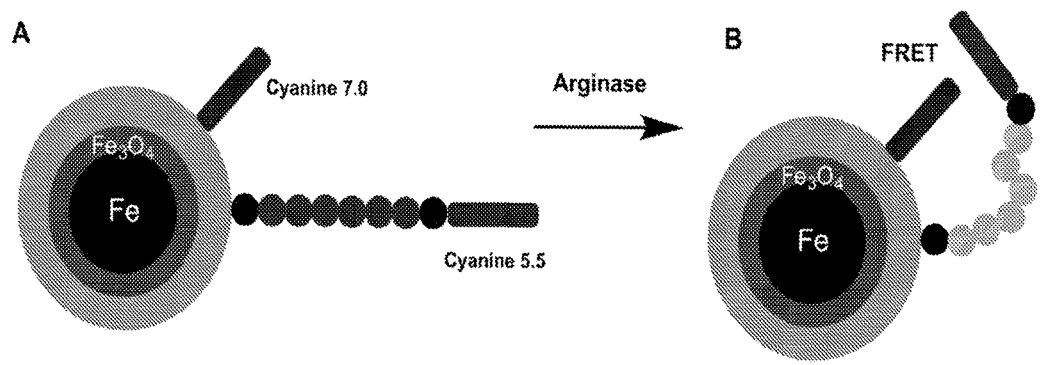
FIG. 10 is a cartoon illustration of an arginase nanoplatform using cyanine 5.5 and cyanine 7.0.

From the fluorescence spectra, dual fluorescence from cyanine 5.5 ($\lambda$max=723 nm) and cyanine 7.0 ($\lambda$max=794 nm) was observed. After incubation with arginase II, an increase in cyanine 7.0 fluorescence was observed, which indicates that FRET increases upon conversion of arginine to ornithine. Notably, the fluorescence of nanoplatform 1 increased after incubation with arginase II. Arginine was capable of forming a complex with a cyanine dye, which resulted in fluorescence quenching. A similar effect is observed here, with the exception that cyanine 5.5 is tethered to $GR_7G$ (SEQ ID NO:5), which results in an "infinite" binding constant. The fluorescence quantum yield of nanoplatform 1 increased upon conversion of arginine to ornithine, because the latter does not form complexes with cyanine 5.5. Complex formation between cyanine 7.0 and arginine is not observed. The mechanism of the assay is illustrated in FIG. 10, where FRET is inefficient before reaction of the tether with arginase II. FRET efficiency increases significantly when virtually all arginine residues in the substrate sequence have to be converted to ornithine.

Figure 11:
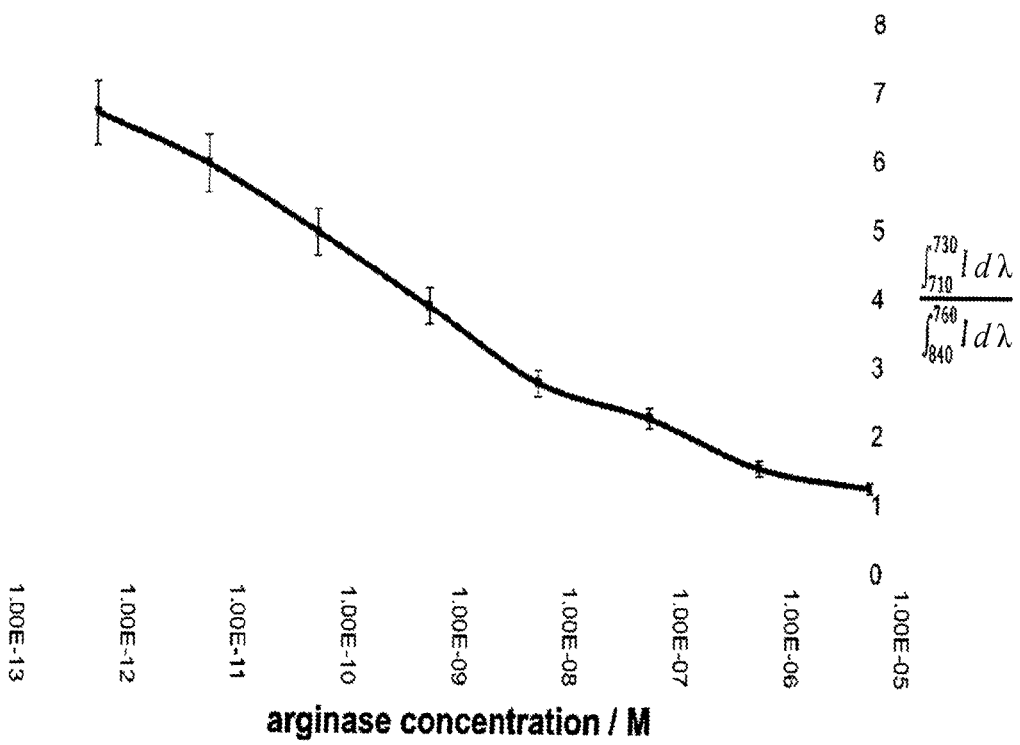
FIG. 11 is a calibration curve of the integrated fluorescence bands of cyanine 5.5 (710 to 730 nm) and cyanine 7.0 (760 to 840 nm) as a function of log 10 of arginase II concentration in Example 3.

Plotting the calibration curve (FIG. 11) shows the quotient of the integrated fluorescence bands of cyanine 5.5 (710 to 730 nm) and cyanine 7.0 (760 to 840 nm) as a function of log 10 of arginase II concentration. The error from three repetitions was determined to 7% (rel.). Based on this error, the LOD (limit of detection) of nanoplatform 1 is down to the picomolar level.

Figure 12:
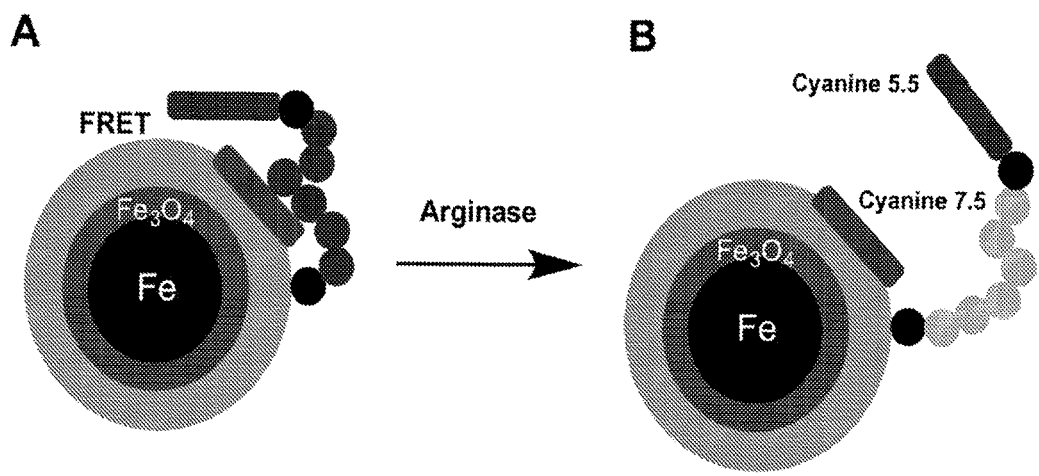
FIG. 12 is a cartoon illustration of an arginase nanoplatform using cyanine 5.5 and cyanine 7.5.

Nanoplatform 2 (FRET pair cyanine 5.5/cyanine 7.5) was tested/calibrated using the same protocols and procedures as described for nanoplatform 1. The only principal difference between the two nanoplatforms is that cyanine 7.5 is tethered to the dopamine coated $Fe/Fe_3O_4$ nanoparticles instead of cyanine 7.0. The most striking difference between the photophysical behaviors of nanoplatforms 1 and 2 is that the latter does not show increased FRET efficiency with increased arginase II concentration and incubation time. For nanoplatform 2, a significant fluorescence increase over the whole observed fluorescence range is observed. This permits the calibration of nanoplatform 2. However, due to the absence of FRET, its LOD is only at $10^{-7}$ M of arginase II concentration, which is two orders of magnitude less than the LOD of nanoplatform 1. The mechanism of the assay is illustrated in FIG. 12.

Figure 13:
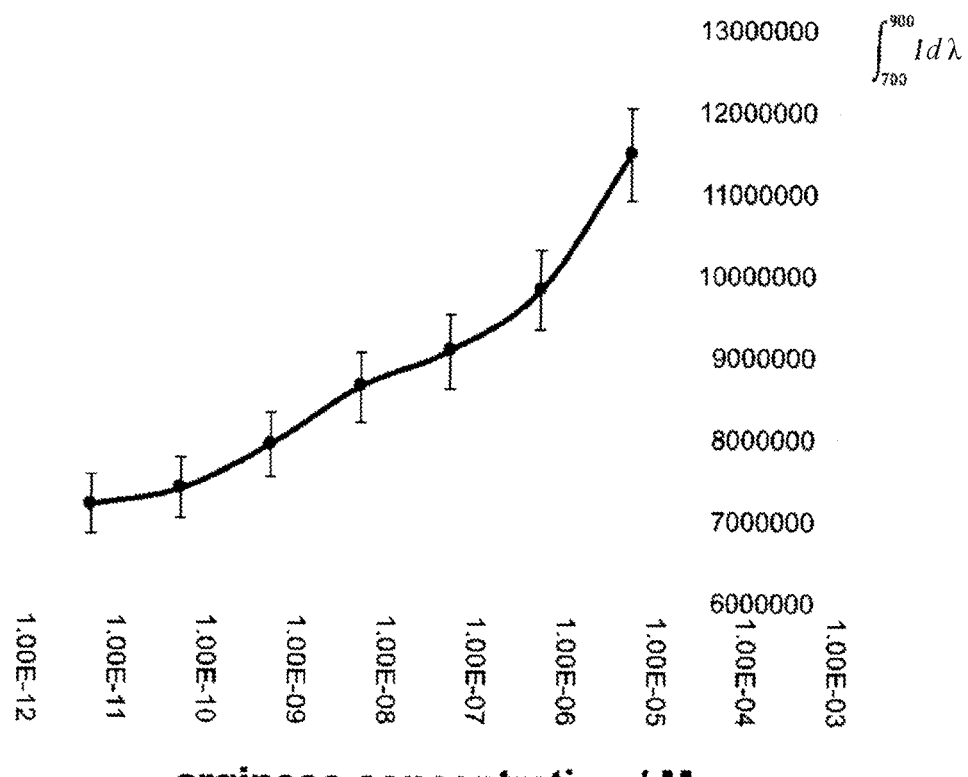
FIG. 13 is a calibration curve of the integrated fluorescence bands of cyanine 5.5 and cyanine 7.5 over the complete fluorescence range (700 to 900 nm) as a function of log 10 of arginase II concentration in Example 3.

Plotting the calibration curve (FIG. 13) for nanoplatform 2 shows the quotient of the integrated fluorescence bands of cyanine 5.5 and cyanine 7.5 over the complete fluorescence range (700 to 900 nm) as a function of log 10 of arginase II concentration. The error from three repetitions was determined to 5% (rel.). Based on this error, the LOD (limit of detection) of nanoplatform 1 is $10^{-10}$ M.

The only chemical difference between cyanine 7.0 and cyanine 7.5 is the existence of two additional fused benzene rings. Apparently, the presence of extended aromatic ring systems in cyanine 7.5 units favors their adsorption at the dopamine-coated interface of the nanoparticles (as depicted in FIG. 12). This enables more efficient fluorescence deactivation of cyanine 7.5 and, therefore, distinctly less fluorescence occurring from cyanine 7.5. However, this does not explain the observed fluorescence increase of nanoplatform 2 with increased arginase II concentration and incubation time. It appears that complex formation between arginine and cyanine 7.5 occurs as well. Notably, FRET between cyanine 5.5 and cyanine 7.5 does not occur after conversion of arginine to ornithine in the substrate sequence. However, the total fluorescence efficiency of both cyanine dyes increases due to reduced complex formation with quaternized organic bases.

Example 4

Arginase Detection in Ex Vivo Tissue Samples

The arginase activity was determined in a syngeneic mouse model for aggressive breast cancer (4T1 tumors in BALB/c mice). Tissue samples of BALB/c mice bearing 4T1 mammary tumors were harvested after the mice were euthanized 26d after tumor initiation in mammary fat pads. The mouse tissue was then homogenized for testing. All measurements of arginase II in tissue samples were performed using 2900 µL of PBS/Dextran, 30 µL of tissue extract and 70 µL of nanoplatform 1 dispersion in PBS/dextran. Assay controls were using 2970 µL of PBS/Dextran and 30 µL of tissue extract. The solutions/dispersions were incubated for 60 min. at 37° C., followed by measuring their fluorescence spectra at 25° C. using a Fluoromax 2 device.

Figure 14:
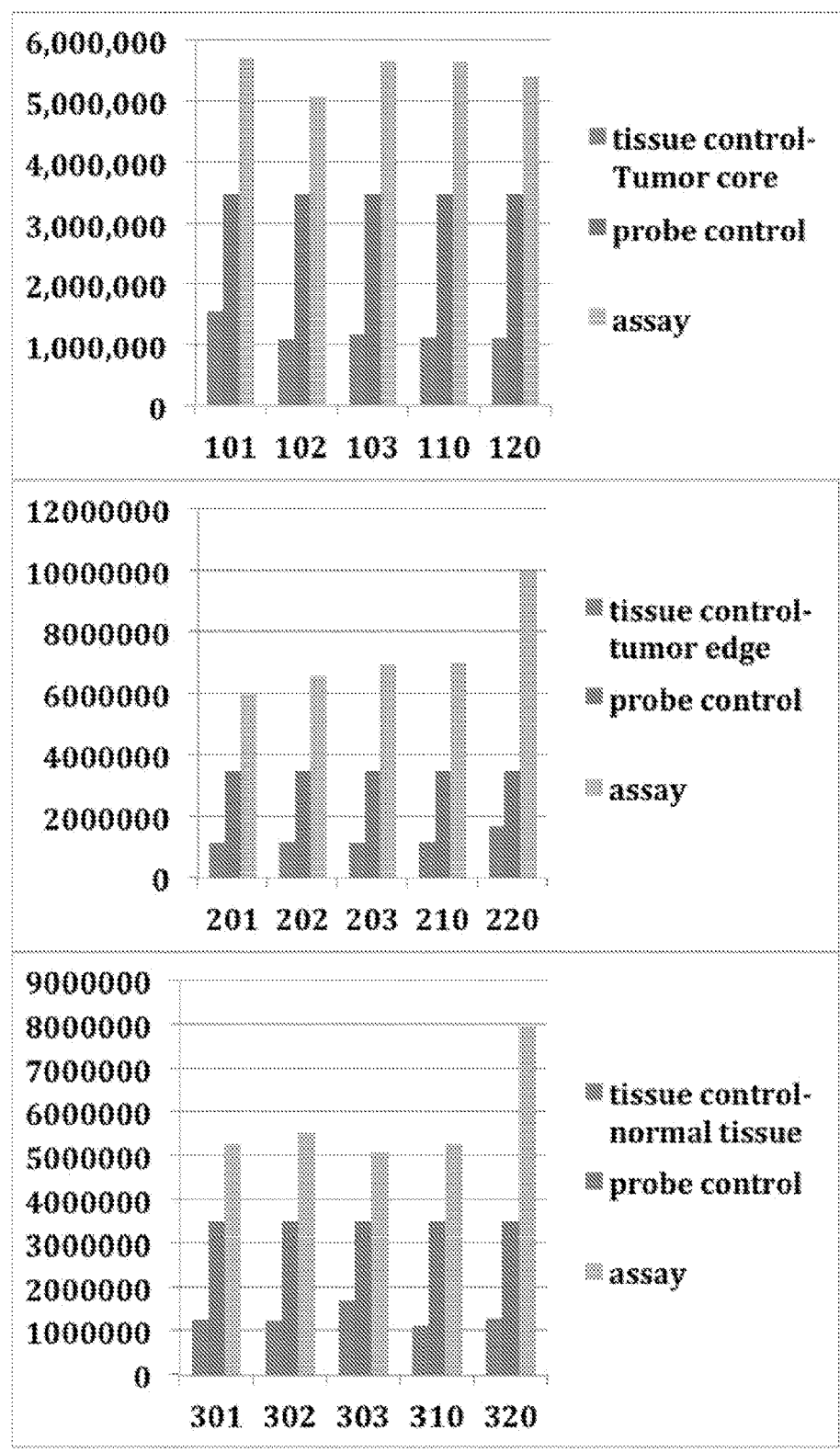
FIG. 14 show graphs from detection of arginase activity in tumor tissue/boundary tissue/"healthy" tissue of 4T1 tumors in BALB/c mice in Example 4, where the Y-axes are the integrated fluorescence intensity and X-axes are the sample numbers.

The results of arginase activity detection in tumor tissue/boundary tissue/"healthy" tissue are shown in FIG. 14, where the Y-axes are the integrated fluorescence intensity and X-axes are the sample numbers. All five tumor core samples show similar fluorescence behavior, which translated into similar arginase II concentrations. The exact concentrations were calculated using the calibration curve for nanoplatform 1. These measurements used of the "ratiometric principle" by monitoring two emission bands at the same time, and then calculating the ratio between them. The major advantage of ratiometric detection methods is that the measurement is becoming virtually independent of the influence of the exact nanoplatform concentration and the biological matrix on the fluorescence measurements.

Four tissue samples from the boundary regions of murine 4T1 tumors resulted in similar photophysical behavior of nanoplatform 1, whereas one tissue sample was clearly different, resulting in a different fluorescence measurement. Since this is a syngeneic mouse model (possessing an intact immune system), it is very likely that one mouse developed a (weak) immune response to the tumor, resulting in a lower local arginase II activity. A comparison between the fluorescence spectra of tumor core samples and tumor boundary samples indicates that the intensity of the fluorescence spectra resulting from each tissue group are different. This may be caused by the presence of different proteins in tumor core and boundary regions. Nevertheless, the ratiometric principle is working well, permitting a direct comparison of the arginase II concentrations in both kinds of tissue.

In the presumably non-cancerous "healthy" regions of murine 4T1 tumors also showed an outlier sample. Most interestingly, the arginase II concentration in the boundary region between tumor and presumably healthy tissue is, on average, 3.5 times higher than in the tumor core region, and 2.2 times higher than in presumably healthy tissue. Comparisons of arginase activities in the samples indicates that immune suppression is most pronounced in the boundary zone where the cancer is invading "normal" tissue. This is of importance for novel approaches to immunotherapy, which have to target the boundary region of a tumor to be successful. There is also a systemic immunodepression effect in cancer, which influences the biochemistry of the whole organism. Although immunodepression is strongest in the boundary region, it is by no means limited to that region.

Example 5

Detection of Arginase Activity in Blood Serum from Cancer Patients

Figure 15:
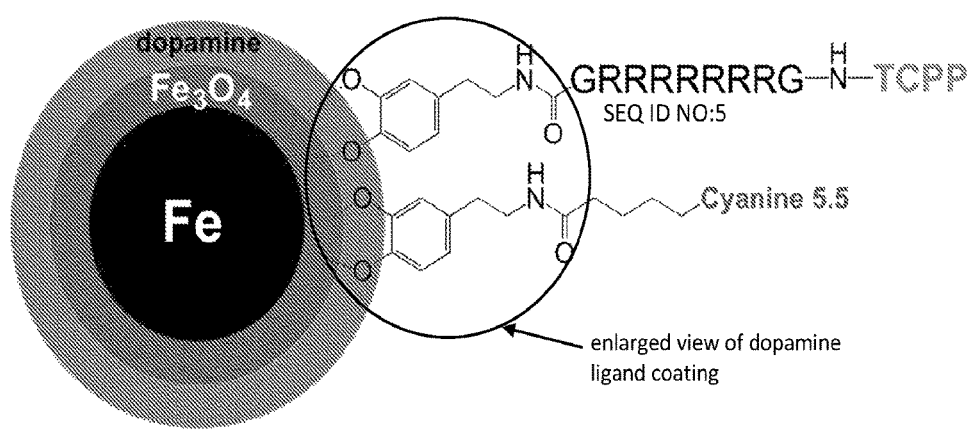
FIG. 15 is an illustration of the arginase nanoplatform used in Example 5 using TCPP as a FRET donor and cyanine 5.5 as a FRET acceptor for detection of arginase activity in serum samples from cancer patients.

Blood serum samples from patients with thyroid, breast, or lung cancer was incubated with the assay. An additional nanoplatform for arginase II detection was designed. In agreement with the nanoplatforms for protease detection, this nanoplatform features the fluorophore TCPP (tetrakis-carboxyphenyl-porphyrin), together with its proven FRET acceptor Cyanine 5.5. The principal structure of this nanoplatform is shown in FIG. 15.

The biospeciments were obtained from Prof. Gaohong Zhu, MD, First Affiliated Hospital of Kunming Medical University, Kunming (Yunnan Province), China. The measurements were following exactly the protocol discussed for nanoplatform I and nanoplatform II, except that human serum instead of mouse tissue extract was used. We have obtained statistically significant differences between presumably healthy patients and patients diagnosed with 12 different solid cancers (all stages I and II). For breast cancer, thyroid cancer, prostate cancer, colorectal cancer, gallbladder cancer, hepatoma and pancreatic head cancer, we have observed a statistically significant increase of arginase II expression in blood. For lung cancer, cervical cancer, ovarian cancer, and fibroid cancer, the arginase II expression of the cancer patients was significantly lower than of the healthy subjects. This observation indicates that the routine observation of arginase II production in serum is a powerful indicator of various tumors. The detection of arginase II can be combined with detection of MMPs 1, 3, 7 and cathepsins B, D, L, and K to detect solid tumors in serum at stages 0 or I.

TABLE

Significance of Arginase II Expression Patterns in Cancer Patients vs. Healthy Human Subjects

| Cancer Type | Arginase II activity in serum of cancer patients is significantly higher than in cancer patients (indication for systemic immunosuppression) | Arginase II activity in serum of cancer patients is significantly lower than in cancer patients (indication of an immune reaction) |
|---|---|---|
| Breast Cancer | 0.0001298 | |
| Lung Cancer | | 0.02953 |
| Cervical Cancer | 0.003013 | |
| Thyroid Cancer | 0.004274 | |
| Endometrial Cancer | | $8.88E^{-11}$ |
| Ovarian Cancer | | 0.00161 |
| Prostate Cancer | 0.01886 | |
| Colorectal Cancer | 0.006037 | |
| Gallbladder Cancer | 0.01697 | |
| Fibroid Cancer | | $1.95E^{-7}$ |
| Hepatoma | 0.2767 | |
| Pancreatic Head Cancer | $5.01E^{-7}$ | |

The numbers in the Table are p-values. They are considered significant when lower than p = 0.05.

Figure 16:
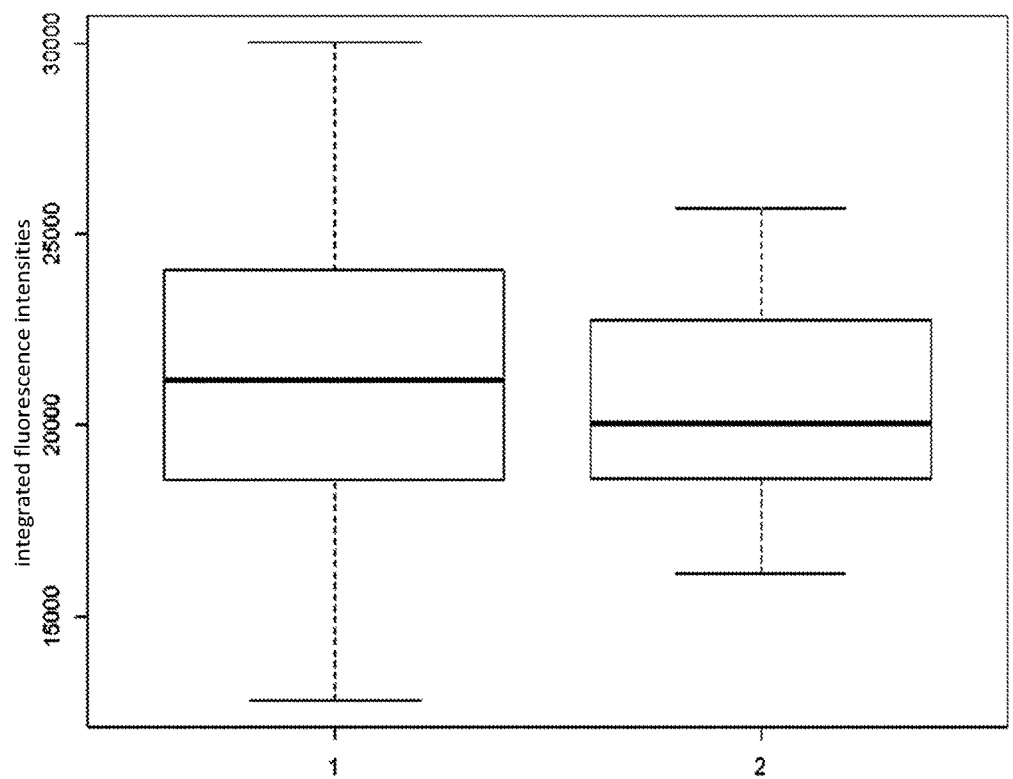
FIG. 16 is a boxplot of the integrated fluorescence intensities (TCPP emission, integrated between 630 and 680 nm) for thyroid carcinoma (#1) as compared to healthy (#2) blood serum.
Figure 17:
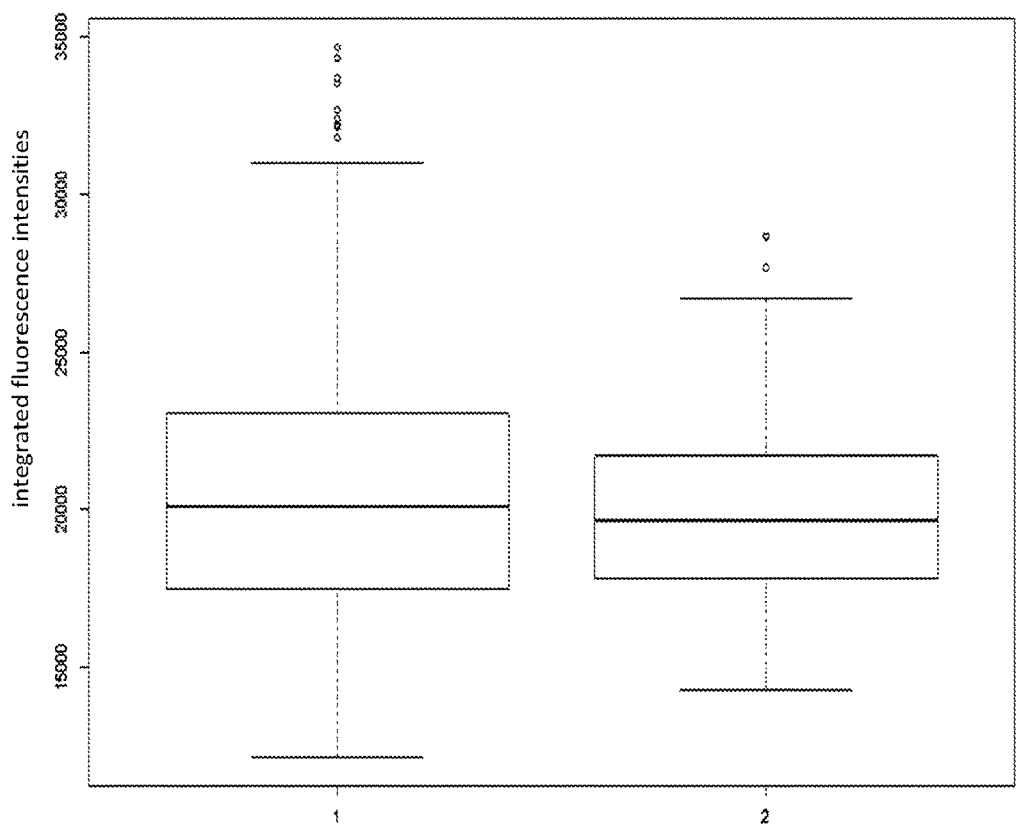
FIG. 17 is a boxplot of the integrated fluorescence intensities (TCPP emission, integrated between 630 and 680 nm) for stage I&II breast cancer (#1) as compared to healthy (#2) blood serum.
Figure 18:
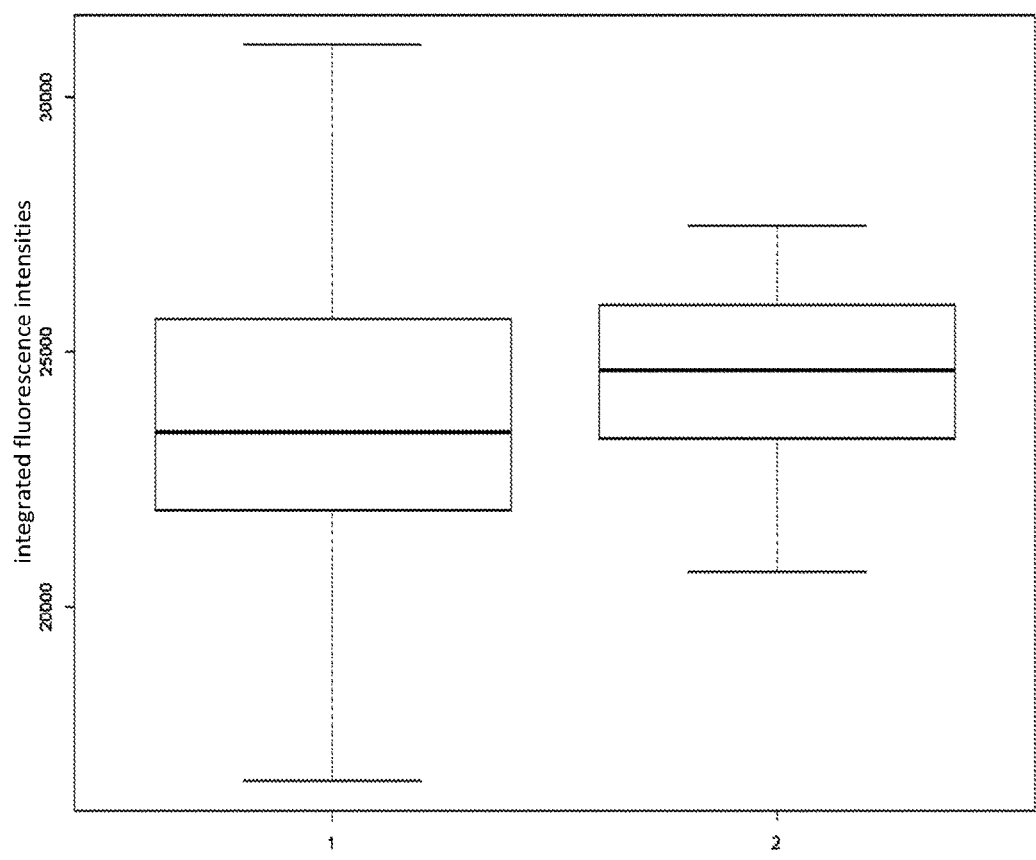
FIG. 18 is a boxplot of the integrated fluorescence intensities (TCPP emission, integrated between 630 and 680 nm) for lung cancer (#1) as compared to healthy (#2) blood serum.

These results demonstrate that the arginase concentration in thyroid and breast cancers are increased, whereas they are decreased in lung cancer, most likely due to inflammation. Data was analyzed using Welch's Two Sample t-test. The analysis is based on approx. 350 breast and thyroid cancer patients, 150 lung cancer patients, and 150 visibly healthy human subjects. FIG. 16 is a boxplot of the results for thyroid carcinoma (#1) as compared to healthy (#2) blood serum. FIG. 17 is a boxplot of the results for stage I&II breast cancer (#1) as compared to healthy (#2) blood serum. FIG. 18 is a boxplot of the results for lung cancer (#1) as compared to healthy (#2) blood serum.

Figure 19:
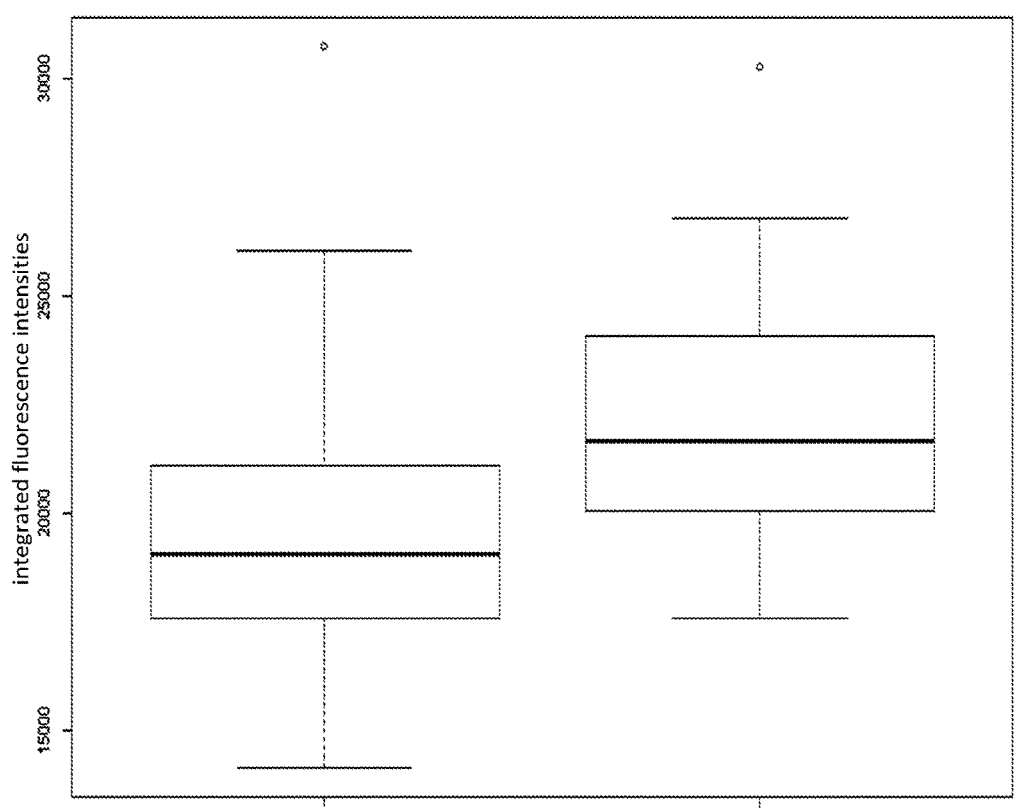
FIG. 19 is a boxplot of the integrated fluorescence intensities (TCPP emission, integrated between 630 and 680 nm) for endometrial cancer (right, 72 female patients) as compared with healthy subjects (left, 55 female patients)

FIG. 19 is a boxplot of the results for endometrial cancer (right, 72 female patients) as compared with healthy subjects (left, 55 female patients).

Figure 20:
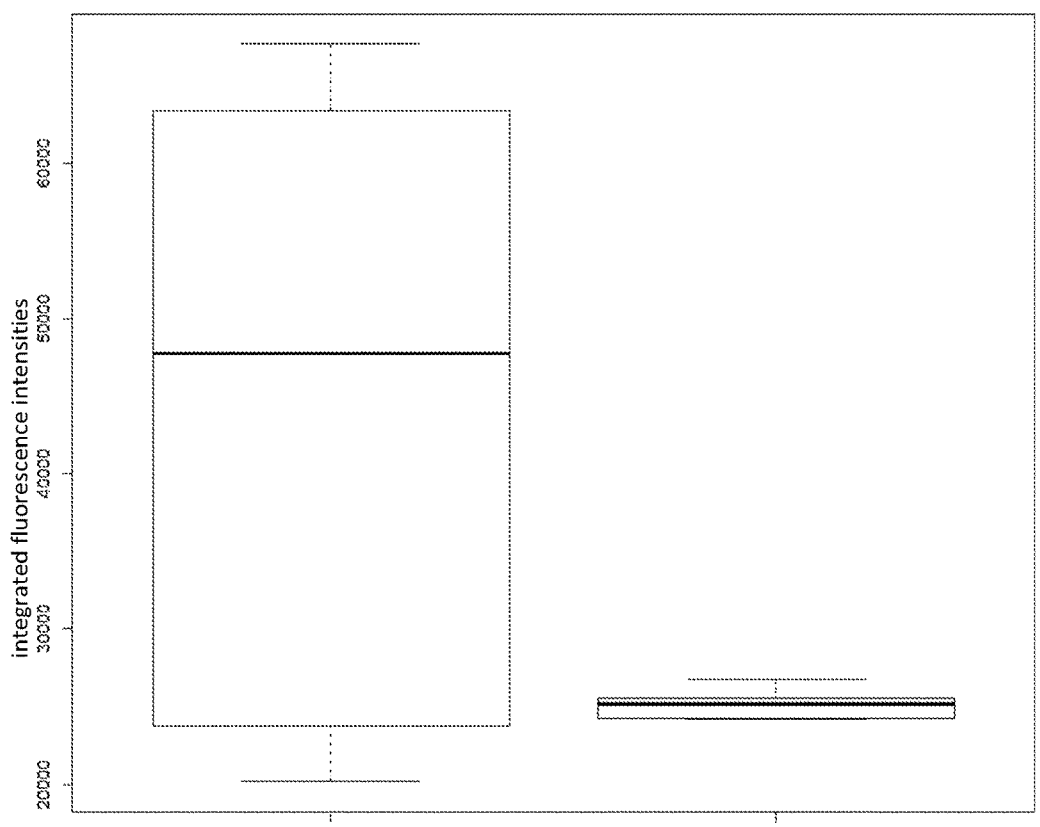
FIG. 20 is a boxplot of the integrated fluorescence intensities (TCPP emission, integrated between 630 and 680 nm) for pancreatic head cancer (right, 42 men, 24 women) as compared to healthy subjects (left, 31 men, 34 women).

FIG. 20 is a boxplot of the results for pancreatic head cancer (right, 42 men, 24 women) as compared to healthy subjects (left, 31 men, 34 women).

The y-axes values are integrated fluorescence intensities (TCPP emission, integrated between 630 and 680 nm).

We claim:

1. A nanoplatform assembly for detecting the presence of an active enzyme in a sample, wherein said enzyme is arginase, said nanoplatform comprising:
   a central carrier particle;
   a first particle;
   a second particle; and
   an oligopeptide linkage connecting said central carrier particle and said second particle,
   wherein said first particle is directly attached to said central carrier particle, and wherein said oligopeptide linkage comprises a substrate sequence for said enzyme, wherein said substrate sequence comprises a sequence according to (I) or (II):

$(X)_n(R)_m(X)_l$ (SEQ ID NO:1),   (I)

where:
   each R: arginine;
   each X: any amino acid;
   m: 3-10;
   n: 1-6; and
   l: 1-6; or $(X)_n(RJ)_m(X)_l$ (SEQ ID NO:2),   (II)

where:
   each R: arginine;
   each X: any amino acid;
   each J: E, A, L, M, K, R, Q, or H;
   m: 2-20;
   n: 1-6; and
   l: 1-6.

2. A nanoplatform assembly for detecting the presence of an active enzyme in a sample, wherein said enzyme is indoleamine 2,3-dioxygenase 1, said nanoplatform comprising:
   a central carrier particle;
   a first particle;
   a second particle; and
   an oligopeptide linkage connecting said central carrier particle and said second particle,
   wherein said first particle is directly attached to said central carrier particle, and wherein said oligopeptide linkage comprises a substrate sequence for said enzyme, said substrate sequence comprises a sequence according to (III) or (IV):

$(X)_n(W)_m(X)_l$ (SEQ ID NO:3),   (III)

where:
   each W: L- or D-tryptophan;
   each X: any amino acid;
   m: 3-10
   n: 1-6; and
   l: 1-6; or $(X)_n(WU)_m(X)_l$ (SEQ ID NO:4),   (IV)

where:
   each W: L- or D-tryptophan;
   each X: any amino acid;
   each U: G, N, D, P, or S;
   m: 2-20;
   n: 1-6; and
   l: 1-6.

3. A nanoplatform assembly for detecting the presence of an active enzyme in a sample, wherein said enzyme is tryptophan 2,3-dioxygenase, said nanoplatform comprising:
   a central carrier particle;
   a first particle;
   a second particle; and
   an oligopeptide linkage connecting said central carrier particle and said second particle,
   wherein said first particle is directly attached to said central carrier particle, and wherein said oligopeptide linkage comprises a substrate sequence for said enzyme, said substrate sequence comprises a sequence according to (III) and/or (IV):

$(X)_n(W)_m(X)_l$ (SEQ ID NO:3),   (III)

where:
   each W: L-tryptophan;
   each X: any amino acid;
   m: 3-10
   n: 1-6; and
   l: 1-6; or $(X)_n(WU)_m(X)_l$ (SEQ ID NO:4),   (IV)

where:
   each W: L-tryptophan;
   each X: any amino acid;
   each U: G, N, D, P, or S;
   m: 2-20;
   n: 1-6; and
   l: 1-6.

4. The nanoplatform assembly of claim 1, comprising a plurality of said first particle and a plurality of said second particle, each of said first particles being directly attached to said central carrier particles, and each of said second particles being connected to said central carrier particle by respective oligopeptide linkages.

5. The nanoplatform assembly of claim 1, wherein said first and second particles are each individually selected from the group consisting of nanoparticles, chromophores/luminophores, quantum dots, viologens, and combinations thereof.

6. The nanoplatform assembly of claim 1, wherein said central carrier particle is a metal or non-metal nanoparticle.

7. The nanoplatform assembly of claim 6, wherein said nanoparticle is a core/shell nanoparticle comprising a metal or metal-alloy core and a metal shell.

8. The nanoplatform assembly of claim 7, wherein said core is selected from the group consisting of Au, Ag, Cu, Co, Fe, and Pt, and said shell is selected from the group consisting of Au, Ag, Cu, Co, Fe, Pt, the metal oxides thereof, and combinations thereof.

9. The nanoplatform assembly of claim 6, wherein said nanoparticle is a stabilized nanoparticle comprising an organic monolayer coating, said first particle being directly attached to said coating.

10. The nanoplatform assembly of claim 2, comprising a plurality of said first particle and a plurality of said second particle, each of said first particles being directly attached to said central carrier particles, and each of said second particles being connected to said central carrier particle by respective oligopeptide linkages.

11. The nanoplatform assembly of claim 2, wherein said first and second particles are each individually selected from the group consisting of nanoparticles, chromophores/luminophores, quantum dots, viologens, and combinations thereof.

12. The nanoplatform assembly of claim 2, wherein said central carrier particle is a metal or non-metal nanoparticle.

13. The nanoplatform assembly of claim 12, wherein said nanoparticle is a core/shell nanoparticle comprising a metal or metal-alloy core and a metal shell.

14. The nanoplatform assembly of claim 13, wherein said core is selected from the group consisting of Au, Ag, Cu, Co, Fe, and Pt, and said shell is selected from the group consisting of Au, Ag, Cu, Co, Fe, Pt, the metal oxides thereof, and combinations thereof.

15. The nanoplatform assembly of claim 12, wherein said nanoparticle is a stabilized nanoparticle comprising an organic monolayer coating, said first particle being directly attached to said coating.

16. The nanoplatform assembly of claim 3, comprising a plurality of said first particle and a plurality of said second particle, each of said first particles being directly attached to said central carrier particles, and each of said second particles being connected to said central carrier particle by respective oligopeptide linkages.

17. The nanoplatform assembly of claim 3, wherein said first and second particles are each individually selected from the group consisting of nanoparticles, chromophores/luminophores, quantum dots, viologens, and combinations thereof.

18. The nanoplatform assembly of claim 3, wherein said central carrier particle is a metal or non-metal nanoparticle.

19. The nanoplatform assembly of claim 18, wherein said nanoparticle is a core/shell nanoparticle comprising a metal or metal-alloy core and a metal shell.

20. The nanoplatform assembly of claim 19, wherein said core is selected from the group consisting of Au, Ag, Cu, Co, Fe, and Pt, and said shell is selected from the group consisting of Au, Ag, Cu, Co, Fe, Pt, the metal oxides thereof, and combinations thereof.

21. The nanoplatform assembly of claim 18, wherein said nanoparticle is a stabilized nanoparticle comprising an organic monolayer coating, said first particle being directly attached to said coating.

\* \* \* \* \*

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: REPEAT
<222> LOCATION: (1)..(1)
<223> OTHER INFORMATION: 1 to 6 residues
<220> FEATURE:
<221> NAME/KEY: REPEAT
<222> LOCATION: (2)..(2)
<223> OTHER INFORMATION: 2 to 9 residues
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: REPEAT
<222> LOCATION: (4)..(4)
<223> OTHER INFORMATION: 1 to 6 residues

<400> SEQUENCE: 1

Xaa Arg Arg Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MISC_FEATURE
```

```
<222> LOCATION: (1)..(1)
<223> OTHER INFORMATION: Xaa is any amino acid
<220> FEATURE:
<221> NAME/KEY: REPEAT
<222> LOCATION: (1)..(1)
<223> OTHER INFORMATION: 1 to 6 residues
<220> FEATURE:
<221> NAME/KEY: REPEAT
<222> LOCATION: (2)..(3)
<223> OTHER INFORMATION: 2 to 20 repeat units
<220> FEATURE:
<221> NAME/KEY: MISC_FEATURE
<222> LOCATION: (3)..(3)
<223> OTHER INFORMATION: Xaa is individually Glu, Ala, Leu, Met, Lys,
      Arg, Gln, or His
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: REPEAT
<222> LOCATION: (4)..(4)
<223> OTHER INFORMATION: 1 to 6 residues

<400> SEQUENCE: 2

Xaa Arg Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: REPEAT
<222> LOCATION: (1)..(1)
<223> OTHER INFORMATION: 1 to 6 residues
<220> FEATURE:
<221> NAME/KEY: REPEAT
<222> LOCATION: (2)..(2)
<223> OTHER INFORMATION: 2 to 9 residues
<220> FEATURE:
<221> NAME/KEY: MOD_RES
<222> LOCATION: (2)..(2)
<223> OTHER INFORMATION: L- or D-Trp
<220> FEATURE:
<221> NAME/KEY: MOD_RES
<222> LOCATION: (3)..(3)
<223> OTHER INFORMATION: L- or D-Trp
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: REPEAT
<222> LOCATION: (4)..(4)
<223> OTHER INFORMATION: 1 to 6 residues

<400> SEQUENCE: 3

Xaa Trp Trp Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MISC_FEATURE
```

```
<222> LOCATION: (1)..(1)
<223> OTHER INFORMATION: Xaa is any amino acid
<220> FEATURE:
<221> NAME/KEY: REPEAT
<222> LOCATION: (1)..(1)
<223> OTHER INFORMATION: 1 to 6 residues
<220> FEATURE:
<221> NAME/KEY: MOD_RES
<222> LOCATION: (2)..(2)
<223> OTHER INFORMATION: L- or D-Trp
<220> FEATURE:
<221> NAME/KEY: REPEAT
<222> LOCATION: (2)..(3)
<223> OTHER INFORMATION: 2 to 20 repeat units
<220> FEATURE:
<221> NAME/KEY: MISC_FEATURE
<222> LOCATION: (3)..(3)
<223> OTHER INFORMATION: Xaa is Gly, Asn, Asp, Pro, or Ser
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: REPEAT
<222> LOCATION: (4)..(4)
<223> OTHER INFORMATION: 1 to 6 residues

<400> SEQUENCE: 4

Xaa Trp Xaa Xaa
 1

<210> SEQ ID NO 5
<211> LENGTH: 9
<212> TYPE: PRT
<213> ORGANISM: Artificial Sequence
<220> FEATURE:
<223> OTHER INFORMATION: Synthetic substrate sequence

<400> SEQUENCE: 5

Gly Arg Arg Arg Arg Arg Arg Arg Gly
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MOD_RES
<222> LOCATION: (2)..(8)
<223> OTHER INFORMATION: Orn

<400> SEQUENCE: 6

Gly Xaa Xaa Xaa Xaa Xaa Xaa Xaa Gly
 1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic substrate sequence

<400> SEQUENCE: 7

Gly Arg Ala Arg Gln Arg Leu Arg Ala Arg Gln Gly
 1               5                  10

<210> SEQ ID NO 8
<211> LENGTH: 16
<212> TYPE: PRT
```

```
<213> ORGANISM: Artificial Sequence
<220> FEATURE:
<223> OTHER INFORMATION: Synthetic substrate sequence

<400> SEQUENCE: 8

Gly Asn Trp Pro Trp Asp Trp Gly Trp Asp Trp Pro Trp Asn Trp Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(5)
<223> OTHER INFORMATION: D-Trp
<220> FEATURE:
<221> NAME/KEY: MOD_RES
<222> LOCATION: (7)..(7)
<223> OTHER INFORMATION: D-Trp
<220> FEATURE:
<221> NAME/KEY: MOD_RES
<222> LOCATION: (9)..(9)
<223> OTHER INFORMATION: D-Trp
<220> FEATURE:
<221> NAME/KEY: MOD_RES
<222> LOCATION: (11)..(11)
<223> OTHER INFORMATION: D-Trp
<220> FEATURE:
<221> NAME/KEY: MOD_RES
<222> LOCATION: (13)..(13)
<223> OTHER INFORMATION: D-Trp
<220> FEATURE:
<221> NAME/KEY: MOD_RES
<222> LOCATION: (15)..(15)
<223> OTHER INFORMATION: D-Trp

<400> SEQUENCE: 9

Gly Asn Trp Pro Trp Asp Trp Gly Trp Asp Trp Pro Trp Asn Trp Gly
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Synthetic substrate sequence
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (8)..(8)
<223> OTHER INFORMATION: Orn
<220> FEATURE:
<221> NAME/KEY: MOD_RES
<222> LOCATION: (10)..(10)
<223> OTHER INFORMATION: Orn
```

<400> SEQUENCE: 10

Gly Xaa Ala Xaa Gln Xaa Leu Xaa Ala Xaa Gln Gly
1               5                   10